(12) United States Patent
Grimes

(10) Patent No.: US 6,359,444 B1
(45) Date of Patent: Mar. 19, 2002

(54) REMOTE RESONANT-CIRCUIT ANALYTE SENSING APPARATUS WITH SENSING STRUCTURE AND ASSOCIATED METHOD OF SENSING

(75) Inventor: Craig A. Grimes, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/322,403

(22) Filed: May 28, 1999

(51) Int. Cl.$^7$ .......................... G01N 22/00; G01N 27/26
(52) U.S. Cl. .................... 324/633; 436/149; 422/82.01
(58) Field of Search ................................ 324/633, 652; 436/149; 422/82.01; 426/231

(56) References Cited

U.S. PATENT DOCUMENTS

| | | | |
|---|---|---|---|
| 4,510,489 A | 4/1985 | Anderson, III et al. ...... 340/572 |
| 4,660,025 A | 4/1987 | Humphrey .................... 340/572 |
| 4,745,401 A | 5/1988 | Montean ...................... 340/572 |
| 4,769,631 A | 9/1988 | Copeland ..................... 340/551 |
| 4,980,670 A | 12/1990 | Humphrey et al. .......... 340/551 |
| 5,339,051 A * | 8/1994 | Koehler et al. .......... 324/652 X |
| 5,348,761 A | 9/1994 | Mitter et al. ................. 427/101 |
| 5,499,015 A | 3/1996 | Winkler et al. .............. 340/551 |
| 5,508,203 A | 4/1996 | Fuller et al. ................. 436/149 |
| 5,514,337 A | 5/1996 | Groger et al. ............ 422/82.08 |

(List continued on next page.)

OTHER PUBLICATIONS

Grate and Abraham, "Solubility interactions and the design of chemically selective sorbent coatings for chemical sensors and arrays," vol. 3 *Sensors and Actuators B*, 1991, pp. 85–111.

Zhou, et al., "Polymer–coated OCR sensors for the detection of organic solvents in water," vol. 35, No. 36 *Sensors and Actuators B*, 1996, pp. 176–182.

Nagasaki, et al., "New Thermosensitive Rubbery Polymers. Synthesis of Poly(siloxyethlene gycol) and Its Aqueous Solution Properties," vol. 29 *Macromolecules*, 1996, pp. 5859–5863.

Grimes, et al., "A Remotely Interrogatable Magnetochemical Ph Sensor," vol. 33, No. 5 IEEE Transactions on Magnetics, Sep. 1997, pp. 3412–3414.

Stoyanov, et al., "A Remotely interrogatable Sensor for Chemical Monitoring," vol. 34, No. 4 IEEE Transactions on Magnetics, Jul. 1998, pp. 1315–1317.

(List continued on next page.)

*Primary Examiner*—Glenn W. Brown
(74) *Attorney, Agent, or Firm*—Macheledt Bales LLP

(57) ABSTRACT

A resonant sensing apparatus for operative arrangement within a test environment to sense an analyte. A sensing structure is included having an antenna in electrical communication with a resonant circuit and a structural element made of a material that selectively responds to the analyte. This sensing structure will resonate at a particular characteristic resonant frequency in the presence of an applied interrogation electromagnetic field and the analyte upon the occurrence of the selective response. A receiver is used for remotely identifying a value for the characteristic resonant frequency by measuring a plurality of values for electromagnetic emission intensity of the sensing structure taken over an operating range of frequencies. A length of a conductive segment of any component of the resonant circuit may also function as the antenna. A method of sensing an analyte with the sensing structure includes arranging the sensing structure within a test environment and applying an interrogation electromagnetic field causing the sensing structure to resonate. A pre-correlation made between a series of resonant frequency values taken for the sensing structure and a corresponding series of analyte sensing values can be used for the sensing.

12 Claims, 10 Drawing Sheets

U.S. PATENT DOCUMENTS

| | | | |
|---|---|---|---|
| 5,538,803 A | | 7/1996 | Gambino et al. ..... 428/694 TM |
| 5,552,778 A | | 9/1996 | Schrott et al. .......... 340/825.34 |
| 5,554,974 A | | 9/1996 | Brady et al. ................. 340/572 |
| 5,563,583 A | | 10/1996 | Brady et al. ................. 340/572 |
| 5,565,847 A | | 10/1996 | Gambino et al. ........... 340/572 |
| 5,571,401 A | | 11/1996 | Lewis et al. ................. 205/787 |
| 5,597,534 A | | 1/1997 | Kaiser ..................... 422/82.08 |
| 5,686,841 A | * | 11/1997 | Stolarczyk et al. .......... 324/635 |
| 5,694,045 A | * | 12/1997 | Ikeda et al. ................. 324/652 |
| 5,698,089 A | | 12/1997 | Lewis et al. ................. 205/787 |
| 5,705,399 A | | 1/1998 | Larue ......................... 436/501 |
| 5,754,110 A | | 5/1998 | Appalucci et al. .......... 340/572 |
| 5,821,129 A | | 10/1998 | Grimes et al. .............. 436/151 |
| 5,841,350 A | | 11/1998 | Appalucci et al. .......... 340/572 |
| 5,859,587 A | | 1/1999 | Alicot et al. ................. 340/572 |
| 6,025,725 A | * | 2/2000 | Gershenfeld et al. ........ 324/652 |

OTHER PUBLICATIONS

Kikuchi, et al., "Glucose–Sensing Electrode Coated with Polymer Complex Gel Containing Phenylboronic Acid," vol. 68, No. 5 *Analytical Chemistry*, Mar. 1, 1996, pp. 823–828.

Sheppard, et al., "Microfabricated conductimetric pH sensor," vol. 28 *Senors and Actuators B*, 1995, pp. 95–102.

Sheppard, et al., "Design of a conductimetric pH microsensor based on reversibly swelling hydrogels," vol. 10 *Senors and Actuators B*, 1993, pp. 73–77.

Gutiérrez, et al., "Magnetoelastic Properties of Some Fe–Rich Fe–Co–Si–B Metallic Glasses," vol. 111 *Phys. Stat. Sol. (a)*, 1989, pp. 279–283.

Barandiarán and Gutiérrez, "Magnetoelastic sensors based on soft amorphous magnetic alloys," vol. 59 *Sensors and Actuators A*, 1997, pp. 38–42.

Barandiarán, et al., "Non–linear behavior of the magnetoelastic resonance in Fe–rich metallic glasses," vol. 5 *Int. J. of Applied Electromagnetics in Materials*, 1994, pp. 75–81.

Sadler, et al., "Micromachined Semi–Encapsulated Spiral Inductors for Microelectromagnetical Systems (MEMS) Applications," Conference Digest, 1997 International Magnetics Conference, pp. ED–05–ED–06.

Roshen, et al., "Effect of Finite Thickness of Magnetic Substrate on Planar Inductors," vol. 26, No. 1 IEEE Transactions on Magnetics, Jan. 1990, pp. 270–271 & 275.

Ng, et al., Appendix A3 "Inductor and Transformer," *Complete Guide to Semiconductor Devices*, Mc. Graw hill, Inc., 1995, pp. 535–537.

Stutzman and Thiele, "Some Simple Radiating Systems," *Antenna Theory and Design*, john Wiley & Sons, Inc., 1981, pp. 79–95, 108–109, 205, 245, 260–262, 270–272, 274, 284, 286, 289.

* cited by examiner

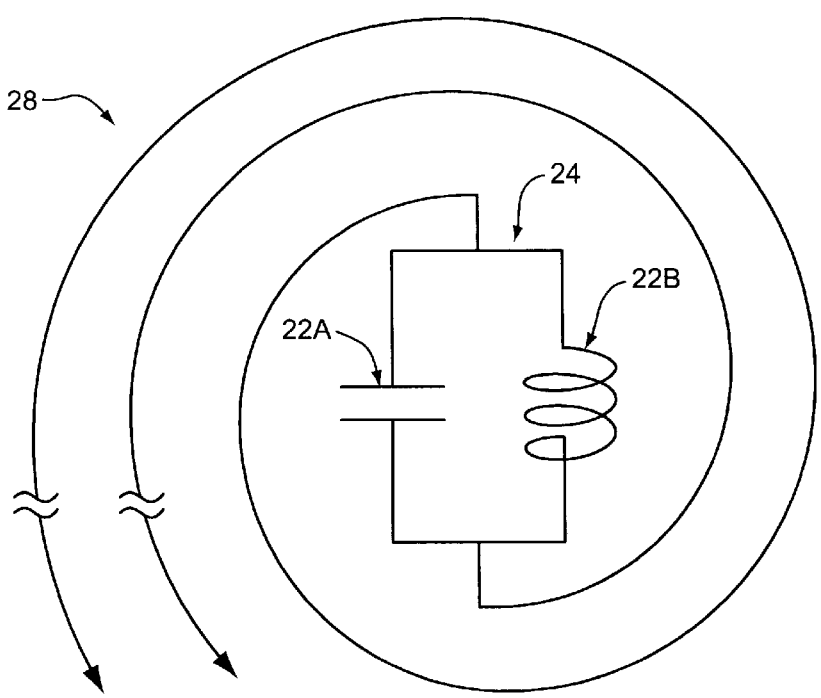
FIG. 4A
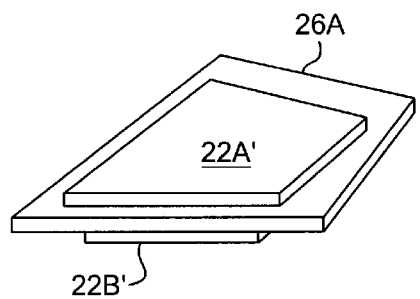
FIG. 4B
FIG. 5
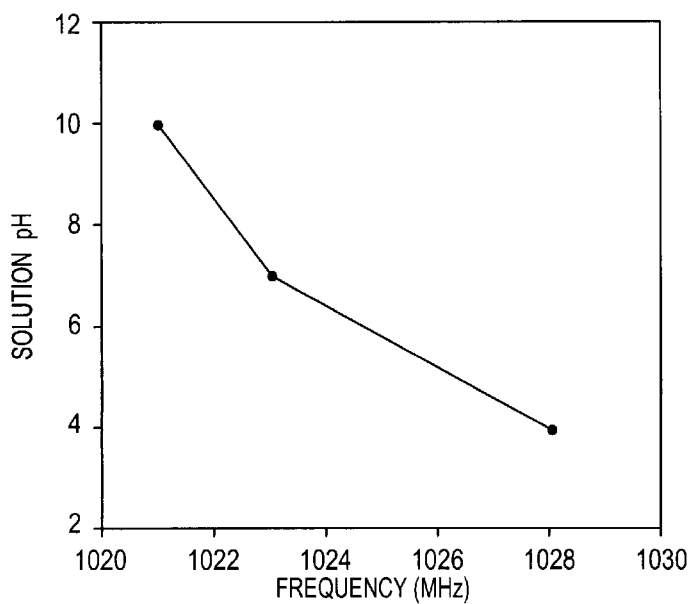

REMOTE RESONANT-CIRCUIT ANALYTE SENSING APPARATUS WITH SENSING STRUCTURE AND ASSOCIATED METHOD OF SENSING

BACKGROUND OF THE INVENTION

The invention disclosed herein may have been produced as a result of work performed under a project funded, in part, by one of the following federal agencies: NASA, NSF, and NIH. As a result, the U.S. Government may have rights to the invention claimed herein. The assignee hereof filed a patent application (Ser. No. 09/223,689) on behalf of the Applicant of the instant patent application, on Dec. 30, 1998 entitled Remote Magneto-elastic Analyte, Viscosity and Temperature Sensing Apparatus and Associated Methods of Sensing. The invention disclosed in both this patent application and the earlier-filed pending patent application (Ser. No. 09/223,689) were invented by Applicant hereof while employed by the assignee.

In general, the present invention relates to telemetry of environmental conditions using sensing devices remotely located from associated pick-up/receiver and processing units for chemical analyte and temperature sensing and monitoring. More particularly, the invention relates to a novel remote radio-frequency (RF) resonant-circuit sensing structure having a structural element made of a material that selectively responds to the analyte or surrounding temperature and associated new sensing apparatus and method of sensing. This novel sensing structure may be used to sense the presence, concentration, or absence of chemical elements and compounds (whether useful or unwanted/ contaminating in a liquid, gas, or plasma state), pH levels, germs (bacteria, virus, etc.), enzymes, antibodies, and so on in a number of environments such as biomedical applications (whether in vivo or in vitro), within medical test samples, food quality/inspection (whether measuring moisture within sealed packing or outside of packaging), monitoring of heavy metals found in water (groundwater, treated water, or wastewater flowing in natural waterways, canals, or pipes), and monitoring of solid or gas manufacturing waste, etc. This new, versatile sensing apparatus and method provides information utilizing a unique remote resonant-circuit recognition technique and sensing structure, whether using one or several such structures positioned within a test environment to provide an array of information.

Known chemical sensing technologies generally require the operation of complex, specifically tailored sensing units, electrically connected, to monitor a target analyte. For example, Groger et al. has a FIG. 4 with a chemically sensitive film 93 positioned between coils 92 and 94 (each of which has been wrapped around a ferrite core); a FIG. 5 with eddy current probes 21 formed by chemical deposition or chemically etching a copper clad printed circuit board (PCB) substrate 11 of a conductive polymer film of polypyrrole, polythiophene or polyaniline which may be deposited directly onto the inductor array or separated by spacers; and a FIG. 6 showing a spiral-wound inductor eddy current probe 13 with a thick film ferrite core 42 deposited on (or etched on) a PCB substrate 12. The Groger et al. probe design is incorporated into an instrument that has a digital signal processor (D)DS) circuit. FIG. 9 illustrates that the probe 83 (such as that in FIGS. 3 or 6) is in electrical connection with, and driven by, sinewave generator 80, preferably a direct digital signal generator, and an op amp 85 to produce a waveform output 86.

Kaiser illustrates a sensor 12, measurement circuit 10 and responder unit 16 coupled to a PCB 22 as an integrated circuit 24 (see FIGS. 1, 2A, and 2B), all contained in a housing 18. The integrated circuit 24 (FIG. 2A) is electrically connected to a sensor electrode 20 and reference electrode 21. The potential difference that develops between the electrodes 20 and 21 in relation to ion concentration, is measured to provide a pH level reading. In FIG. 2B, the sensor 12 of integrated circuit assembly 24 is a temperature sensor which is completely sealed within housing 18. FIGS. 3, 4, and 5 illustrate measurement circuit 10 embodiments: In 3 and 4, a voltage follower 44 outputs a signal proportional to the potential difference detected at sensor 12; FIG. 5 illustrates a familiar Wheatstone bridge with an AC generator 200 powered by an interrogation signal sent by interrogation unit 14. In operation (FIGS. 1 and 6), the RP transmitting and receiving circuitry 64 of interrogation unit 14, transmits an inquiry signal. Sometime thereafter, upon detecting its proper responder unit address, the responder unit 16 transmits data from the measurement circuit 10 back to interrogation unit circuitry 64.

Lewis et al. describes an analog of the mammalian olfactory system (i.e., electronic-nose) having chemiresistor elements micro-fabricated onto a micro-chip. Each sensor has at least first and second conductive leads electrically coupled to and separated by a chemically sensitive resistor (FIG. 4A-1). Each resistor has a plurality of alternating nonconductive and conductive regions transverse to the electrical path between the conductive leads. The chemiresistors are fabricated by blending a conductive material with a nonconductive organic polymer such that the electrically conductive path between the leads coupled to the resistor is interrupted by gaps of non-conductive organic polymer material. See, column 3, lines 38–50. Lewis et al. describes this as "electronic noses, for detecting the presence of an analyte in a fluid" (col. 8). An electronic smelling system according to Lewis et al. (col. 7) has sensor arrays in electrical communication with a measuring device for detecting resistance across each chemiresistor, a computer, a data structure of sensor array response profiles, and a comparison algorithm.

The applicant hereof, in conjunction with others, developed a magneto-chemical sensor comprised of a thin polymeric spacer layer made so that it swells in the presence of certain stimuli, bounded on each side by a magnetically soft thin film, as described in an article co-authored by the applicant entitled A Remotely Interrogatable Magnetochemical pH Sensor, IEEE TRANSACTIONS ON MAGNETICS, VOL. 33, No. 5, SEPTEMBER 1997. When placed within a sinusoidal magnetic field the sensor generates a series of voltage spikes in suitably located detecting coils. The magnetic switching characteristics of the sensor are dependent upon the thickness of the sandwiched intervening polymeric spacer layer. The sandwiched "chemical transduction element" of this magnetism-based technology was made of a lightly crosslinked polymer designed to swell or shrink with changes in the concentration of the species to be sensed. The magnitude of each of the voltage spikes generated by the sensor is dependent upon how much the sandwiched spacer layer has swollen in response to the given stimuli. This sensor can be used with interrogation and detection electronics commonly used in magnetic anti-theft identification marker systems.

In a subsequent structurally-modified magnetochemical sensor developed by the applicants hereof, with others (A Remotely Interrogatable Sensor for Chemical Monitoring, IEEE TRANSACTIONS ON MAGNETICS, VOL. 34, No.4, JULY 1998), a thin film single or array of magnetostatically coupled magnetically soft ferromagnetic thin film structure(s) is adhered to a thin polymeric layer made so that it swells or shrinks in response to a chemical analyte. The sensor is placed within a sinusoidal magnetic field and the magnetization vector of the magnetically soft coupled sensor structures periodically reverses direction generating a magnetic flux that can be remotely detected as a series of voltage spikes in pick-up coils. The four-square array is of magnetically soft thin structures bonded to a polymeric base-substrate layer with acrylate acetate (SUPERGLUE®) and baked. When the swellable base swells (low pH): the distance between the square magnetically soft structures enlarges resulting in less coupling between these structures. If immersed in high pH: this base shrinks as does the distance between structures resulting in a larger voltage signal.

Resonant circuitry has been used in the security tags/markers of electronic article surveillance (EAS) systems that merely detect the presence of an activated tag passing through an interrogation zone of a retail store exit. An EAS tag of this sort affixed to a retail item, which has not been deactivated by a checkout clerk indicating the item has been paid-for, sounds an alarm. For example, Appalucci et al. illustrates such a security tag having a dielectric substrate. The circuit elements of a resonant circuit 12 are formed on both principal surfaces of the substrate 14 by patterning conductive material. The security tag 10 may be deactivated by changing the resonant frequency so that the tag resonates outside of the predetermined detection frequency or by altering the circuit 12 so that it no longer resonates at all. A later patent to Appalucci et al. illustrates another such security tag having a dielectric substrate 14 onto which electrical elements are also patterned to form a resonant circuit 12. Semiconductive electrical parallel connections (bridges) made across bottom and top plates of capacitors $C_1$ and $C_2$ stabilize the resonant tag from electrostatic discharge but still permit the tag to be activated and deactivated. The semiconductive antistatic material comprises a polymer carrier with an ionizable salt dissolved therein to provide resistivity ($10^3$ to $10^8$ ohms per square). The function of the antistatic material is to provide electrical drain-off bridges for the capacitors $C_1$ and $C_2$ to prevent damage thereto. Characteristics of the antistatic carriers include being nontoxic, substantially nonaqueous, substantially neutral in pH, capable of being applied as a thin coating or layer onto a resonant circuit using conventional coating techniques, and compatible with a release sheet and/or adhesive layer applied over the resonant tag circuit (for affixing to an item).

Alicot et al. illustrates a high frequency radio frequency identification (RFID) security tag suited for providing data about the article to which such a tag is attached. This tag has a transponder 18 comprising an RFID chip 20 and an antenna 22 positioned on surface 14 of cover 12. RFID chip 20 contains logic and memory about the article to which it will be attached. A different patent issued to Montean describes another such security marker for use in radio frequency EAS systems.

Other widely used anti-theft markers/tags (electronic article surveillance, EAS, markers) generally operate by "listening" for acoustic energy emitted in response to an interrogating ac magnetic field, to sense the presence of a magnetostrictive EAS marker. Sensormatic, Inc. distributes an EAS tag (dimensions 3.8 cm×1.25 cm×0.04 mm) designed to operate at a fixed frequency of 58 kHz (well beyond the audible range of human hearing). These EAS tags are embedded/incorporated into articles for retail sale. Upon exiting a store, a customer walks through a pair of field coils emitting a 58 kHz magnetic field. If a tag is still in an article being carried by the customer, the tag will likewise emit a 58 kHz electromagnetic signal that can be detected using a pickup coil, which in turn may set off an audible or visual alarm. More-recently, these tags are being placed in a box-resonator, sized slightly larger than the tag, such as the tags placed within a cavity 20 of a housing (FIG. 2 of Winkler et al.).

Therefore, a versatile robust chemical sensor is needed that for obtaining information about an environmental condition (including presence, concentration, temperature, and so on of an analyte) in various diverse test samples/environments through remote query, without requiring direct electrical connection to a receiving device and without the need for specifying sensor orientation.

The new compact sensing structure, sensing apparatus, and associated method of sensing, described herein, are designed for operation within a wide range of test environments whether one-time, periodic (timed or random), or continuous on-going monitoring of a particular analyte or environment is desired. The innovative sensing structure, apparatus, and method utilize a unique resonant-circuit selective recognition technique to sense and measure minute quantities of a selected analyte in gas or liquid phase without requiring sophisticated equipment and without requiring a great deal of space. Furthermore, this new sensing apparatus can be installed/positioned and removed with relative ease and without much disruption of the test sample or test environment. The unique recognition techniques employed by the new sensing apparatus and method include: continuous emission, over a set period of time, of an interrogation field from a source (whether that source is incorporated into the receiving unit or into the sensing structure); radiating shortened pulses (timed or random) of information from the sensing structure to measure its characteristic resonant frequency, as well as radiating shortened interrogation field pulses using a source (whether that source is incorporated into the receiving unit) and listening for the sensing structures response.

If need be, the sensor may be fabricated as a micro-circuit for use in vitro, in vivo, within small-sized sealed packaging or medical test samples (e.g., a test tube), and so on. A micro-sensor can be used where space is limited, and/or it is desired that the tiny sensor be positioned further into the interior of the sample or environment being tested/monitored. And, whether or not built on a larger scale, the novel resonant-circuit sensor can be used for sensing within buildings, rooms of buildings, or other spaces through which contaminant gas passes such as a smokestack or exhaust pipe, for sensing waterways to measure metals contamination, and so on.

The new analyte sensing apparatus and associated methods were developed to utilize space more efficiently while at the same time provide sufficient chemical sensitivity. Unlike the chemical sensing units available and known EAS systems, the sensing apparatus and methods incorporate a unique sensing structure that has a resonant circuit in electrical communication with an antenna, the antenna and/or at least one component of the resonant circuit having a structural element made of a material that selectively responds to an analyte within the test environment. The structural element can be made of a wide variety of materials depending upon the type of sensing information needed and upon the selective interaction, reaction, or response that will result in a measurable change in frequency characteristics of the sensing structure. And, the structural element can be applied to, adhered to, etched to accommodate, sandwiched between, and so on, the resonant circuit component(s) and the antenna. As can be further appreciated, within the spirit and scope of the design goals and as further described herein, the selectively responsive components of the resonant circuit and the antenna associated therewith can be fabricated from micro-components or can be built on a larger scale and formed into many different shapes of many suitable materials; and several such sensors can be incorporated into an array to provide a package of sensing information about one analyte or several analytes within a test environment.

SUMMARY OF THE INVENTION

It is a primary object of this invention to provide an apparatus and associated method for detecting the presence, absence, and/or measuring the amount of an fluid analyte (whether in liquid or gas form), as well as sensing the temperature thereof. A sensing structure (sensor) is used that has an antenna in electrical communication with a resonant circuit, at least one component of which (and/or the antenna) has a structural element made of a material that selectively responds (chemically, thermally, etc.) to the analyte to provide sensing information. It is also an object of this invention that such an apparatus and method utilize electromagnetic emission measurements of the sensing structure remotely taken over a range of successive interrogation frequencies, to perform the sensing/detecting. It is also an object of this invention to provide such a sensing structure that needs no direct hard-wire connection to any field generating coil used or its emission receiving coil, but rather, is remotely located for sensing.

The advantages of providing the new sensing apparatus and associated new method, as described herein, are as follows:

(a) The invention can be used for one-time (whether disposable) operation, periodic, or continuous on-going monitoring of environmental conditions;

(b) Versatility—The invention can be used for operation within a wide range of testing environments such as biomedical applications (whether in vivo or in vitro), within medical test samples, food quality/inspection (within or outside of sealed packing), monitoring of contaminants in water (groundwater, treated water, or wastewater flowing in natural waterways, canals, or pipes), and monitoring of gases/aerosols; The sensing structure can be driven (to resonate) by its own battery and timing circuit or current may be induced in the sensing structure by an EM field(s) generated using a remote coil;

(c) Simplicity of use—The new sensor structure can be installed/positioned and removed with relative ease and without substantial disruption of a test sample/ environment;

(d) Structural design flexibility—The sensor may be formed into many different shapes and may be fabricated as a micro-circuit for use where space is limited and/or the tiny sensor must be positioned further into the interior of a sample or environment being tested/ monitored;

(e) Structural element design for sensing speed—An outer layer(s) or base substrate layer of chemically or thermally responsive material may be shaped, sized, adhered, etched, and so on, to maximize the speed at which the material responds (resulting in a change in characteristic resonant frequency of the sensing structure), allowing the sensor to provide useful information at a faster rate;

(f) Several sensors may be positioned, each at a different location within a large test environment, to sample each of the different locations, simultaneously or sequentially;

(g) Several sensors may be incorporated into an array to provide a package of sensing information about an environment, such as, analyte composition, concentration of constituent components/elements of the analyte, and temperature of the environment in which the analyte(s) is found;

(h) Receiving unit design flexibility—One unit having the capacity to generate an interrogation field, as needed, as well as the capacity to receive electromagnetic waves emitted from several sensing structures, each having a characteristic operating range of resonant frequencies, positioned within the test environment may be used. This wide-band capability requires either the use of broadband antennas, such as spiral antennas, or multiple narrowband transmitting and receiving antennas; see for example the useful antenna design resource entitled "Antenna Theory and Design," by Warren L. Stutzman and Gary A. Thiele, for discussions on antenna design and bandwidth.

(i) Apparatus design simplicity—Reducing the number and size of components required to build a sensing apparatus can reduce overall fabrication costs and add to ease of operation; for example, if the resonant circuit and its associated antenna are electrically connected to an independent, portable power source (such as a small battery and suitable timing circuit), EM waves containing valuable sensing information can be emitted therefrom without needing a separate interrogation field generation coil; and (j) Sensor materials and size can be chosen to make one-time, disposable use economically feasible.

Briefly described, the invention includes a resonant sensing apparatus for operative arrangement within a test environment to sense an analyte. The apparatus comprises: a sensing structure having an antenna in electrical communication with a resonant circuit at least one component of which has a structural element made of a material that selectively responds to the analyte; this sensing structure will resonate at a particular characteristic resonant frequency in the presence of an interrogation electromagnetic field upon the selective response; and a receiver for remotely measuring a value for the characteristic resonant frequency. At least one component may be resistive, capacitive, and inductive in nature such that the selective response causes a change in electrical characteristics of the at least one component resulting in a change in frequency characteristics of the resonant circuit. The components of the resonant circuit can be chosen such that the characteristic resonant frequency is a function of an inductance value of one component and a capacitance value of another component. Additional such sensing structures may be incorporated into an ordered array to provide a package of sensing information—each of the sensing structures designed (shape, size, material) to operate at a different characteristic resonant frequency for detection thereof.

The structural element may take the form of a myriad of different structural shapes of many suitable materials (e.g., electric dielectrics, magnetic dielectrics, chemically responsive alloys, a sorbent polymer film selected from the group consisting of a poly(isobutylene), ethylene-propylene rubber, poly(isoprene), and poly(butadiene) film, a polymer hydrogel having a plurality of microspheres reactive to electrostatic forces of subatomic particles within the analyte, a structure with an outer zeolite layer, a thin outer layer sputtered onto the antenna, etc.), depending upon the desired selective response of this element to the analyte and/or to the environment surrounding the sensor. For example, the structural element may contain a plurality of ferromagnetic elements embedded within a polymeric material located in proximity of windings (whether or not planar) of an inductor. Furthermore, the selective response of the structural element may comprise a myriad of responses such as swelling, causing relocation of these ferromagnetic elements, which in turn changes the magnetic permeability of the inductor, thus affecting an inductance value of the inductor; or an interaction with the analyte resulting in a change in material stiffness of the structural element; or interaction with the analyte causing a change in relative permittivity of a dielectric material (permittivity: $\in = \in_{0(permitivity\ in\ free\ space)}*$dielectric constant), thus, affecting a capacitance value of the at least one component; or a thermal response to the analyte for sensing a temperature thereof (the material being thermally-sensitive, for example, a thin outer layer bonded/adhered to one of the components of the resonant circuit or to the antenna volumetrically expands in response to a temperature change); or, if the material is a chemically receptive polymer, the selective response could comprise absorption of subatomic particulate matter from the analyte; or, if the material is a chemically receptive porous polymer, selective response can comprise interaction with the analyte causing a change in magnetic permeability of the at least one component; and so on.

The component(s) of the resonant circuit may have a myriad of structures, too. One of the components of the resonant circuit can comprise a conductive segment (of many suitable shapes and sizes), wherein at least a length of this conductive segment functions also as the antenna. And, in the event at least a part of the structural element is bonded to this length, the selective response would cause a change in electrical characteristics of the antenna. One of the components may comprise electrically-isolated first and second conductive segments (whether relatively planar, flat-plate, looped, and/or concentric) between which at least a portion of the structural element is located. The first conductive segment may be a relatively planar spiral (which also functions as an inductor for the resonant circuit) adhered to a first surface of the structural element.

The receiver can include a pick-up coil/antenna capable of measuring a plurality of successive values for electromagnetic emission intensity of the sensing structure taken over an operating range of successive interrogation frequencies; this operating range to include the characteristic resonant frequency value of the sensing structure. The resonant frequency value detected will correspond to the relative maximum of the plurality of successive values for electromagnetic emission intensity measured. The receiver's pick-up coil/antenna can be wired in communication with a frequency analyzer. The interrogation electromagnetic field may comprise a pulse of electromagnetic energy emitted just prior to each resonant frequency value measurement taken, or could include pulses emitted, successively, at predetermined intervals. The receiving unit (especially, if intended for portable-field use) may include a battery of some sort (such as an electrochemical cell) coupled to a timing circuit allowing a transmission coil/antenna to emit a series of EM pulses. It may be desirable to couple the sensing structure's antenna to a battery of some sort (such as an electrochemical cell) and a timing circuit allowing it to emit pulses at pre-determined intervals for remote measurement thereof by the receiver. A pre-correlation made between a series of resonant frequency values taken for the sensing structure and a corresponding series of analyte sensing values can be used for the sensing (including sensing concentration, presence/absence of the analyte, temperature, moisture content, pH, etc.). For example, a pre-correlation made between a series of resonant frequency values for the sensing structure and a corresponding series of temperature values for this particular sensing structure can be used by the apparatus of the invention for sensing a temperature.

Additionally, an on-off switch comprising a ferro-electric element, permanently located in proximity to the at least one component of the resonant circuit, may be included with the apparatus. Furthermore, at least one component of the resonant circuit may comprise a magnetizable on-off switch made of a magnetically hard element which, when activated, causes the characteristic resonant frequency to fall outside of a predetermined operating range of frequencies.

Another resonant sensing apparatus having a receiver for remote measurement, as characterized herein, includes: a sensing structure operatively arranged within a test environment comprising an antenna in electrical communication with a resonant circuit having first and second components bonded to a structural element made of a material that selectively responds to the analyte in a manner that changes the frequency characteristics of said resonant circuit; and as before, sensing structure resonates at a characteristic resonant frequency in the presence of an interrogation electromagnetic field upon the selective response. Another resonant sensing apparatus, as characterized herein, includes a sensing structure comprising an antenna in electrical communication with a resonant circuit, the antenna comprising a structural element that selectively responds to the analyte causing a change in electrical characteristics of the antenna.

Within the spirit and scope of the invention, characterizations of a novel method of sensing an analyte with a sensing structure having an antenna in electrical communication with a resonant circuit are included herein. One such method characterization comprises the steps of: applying an interrogation electromagnetic field causing the sensing structure to resonate, at least one component of the resonant circuit comprising a structural element made of a material that selectively responds to the analyte; and remotely measuring, with a receiver, a value for a characteristic resonant frequency of the sensing structure upon its resonating and the selective response. Another such characterization includes: operatively arranging the sensing structure within a test environment, the antenna to comprise a structural element that will selectively respond to the analyte causing a change in electrical characteristics of the antenna; applying an interrogation electromagnetic field causing the sensing structure to resonate at a characteristic resonant frequency upon the selective response; and remotely measuring a value for characteristic resonant frequency.

The unique additional features of the apparatus, as described above, also apply to the characterizations of the method of the invention. These distinguishing features include, but are not limited to: the resonant circuit component(s) features; the receiver's features; the interrogation field alternatives and associated radiating/emission thereof; features of the structural element and its material; the myriad of selective responsiveness alternatives of the structural element; the remote measurement of resonant frequency values; the pre-correlation of a series of resonant frequency values taken for the sensing structure and corresponding series of analyte sensing values; the application of a known mathematical relationship(s) to find values that change after selective response; the operative arrangement of a second sensing structure (having a second antenna in electrical communication with a second resonant circuit, wherein a second structural element selectively responds to the analyte, such that a value for a second characteristic resonant frequency of this second sensing structure, upon its resonance and selective response, can be found); and so on.

BRIEF DESCRIPTION OF THE DRAWINGS

The invention will be more particularly described by referencing the accompanying drawings of the preferred and alternate preferred embodiments and graphical representation of data, in which like numerals designate like parts.

FIG. 4A is a schematic of a sensing structure that incorporates a spiral antenna in electrical communication with resonant circuit components connected in parallel.

FIG. 4B is an isometric view of an alternate preferred sensing structure providing some detail of how selectively responsive material can be sandwiched between components.

FIG. 5 is a graphical representation of resonant frequency of a sensing structure built like that shown in FIG. 4A, as plotted against sensing values (here, pH of an analyte solution) where the structural element was made of a pH responsive polymer.

FIG. 7 is a plot of $f_r$ (resonant frequency the sensing structure behaving as a reflector) vs. $f_0$ (frequency of the resonant LC circuit, measured at its terminals); and FIGS. 8 and 9 are frequency spectrum graphs for the sensing structure illustrating emission intensity peaks for the computer simulated sensing structure at $f_r$=668 MHz and at $f_r$=685 MHz (interrogation frequency values are shown along the x-axis in both graphs).

DETAILED DESCRIPTION OF THE PREFERRED EMBODIMENTS

Figure 1A:
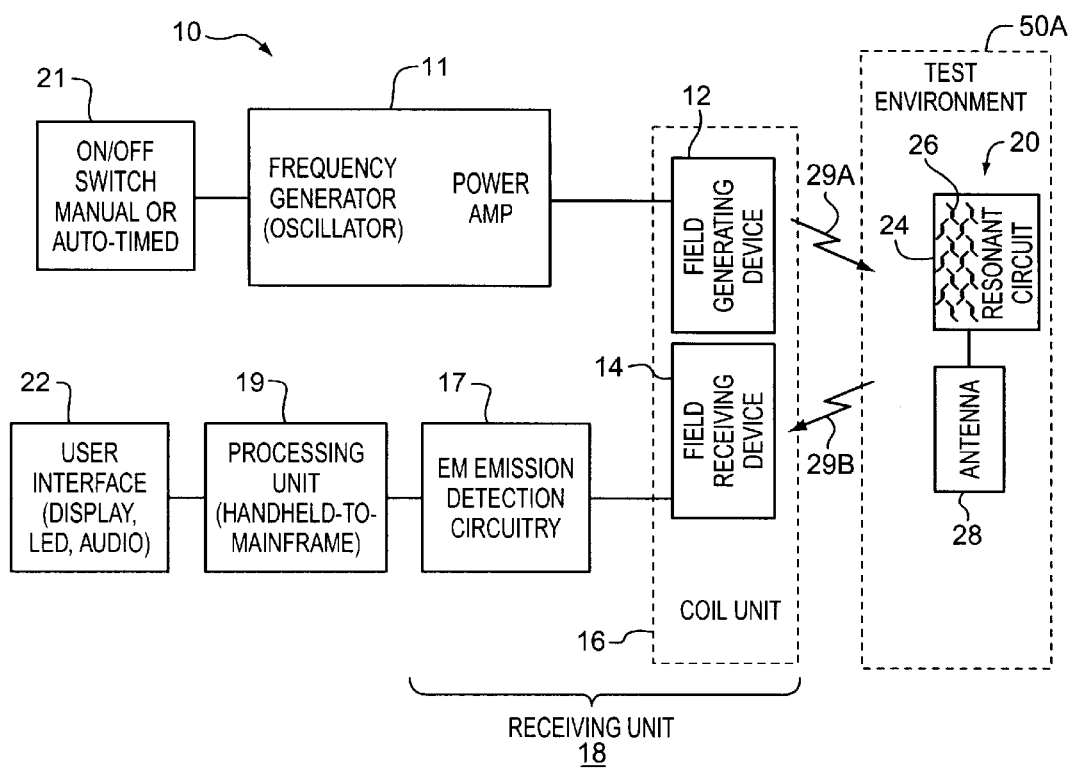
FIGS. 1A and 1B illustrate preferred sensing apparatuses of the invention in schematic-block diagram form. A sensing structure similar to any of those depicted in FIGS. 2A–2E may, also, be operatively arranged within the test environment defined.
Figure 1B:
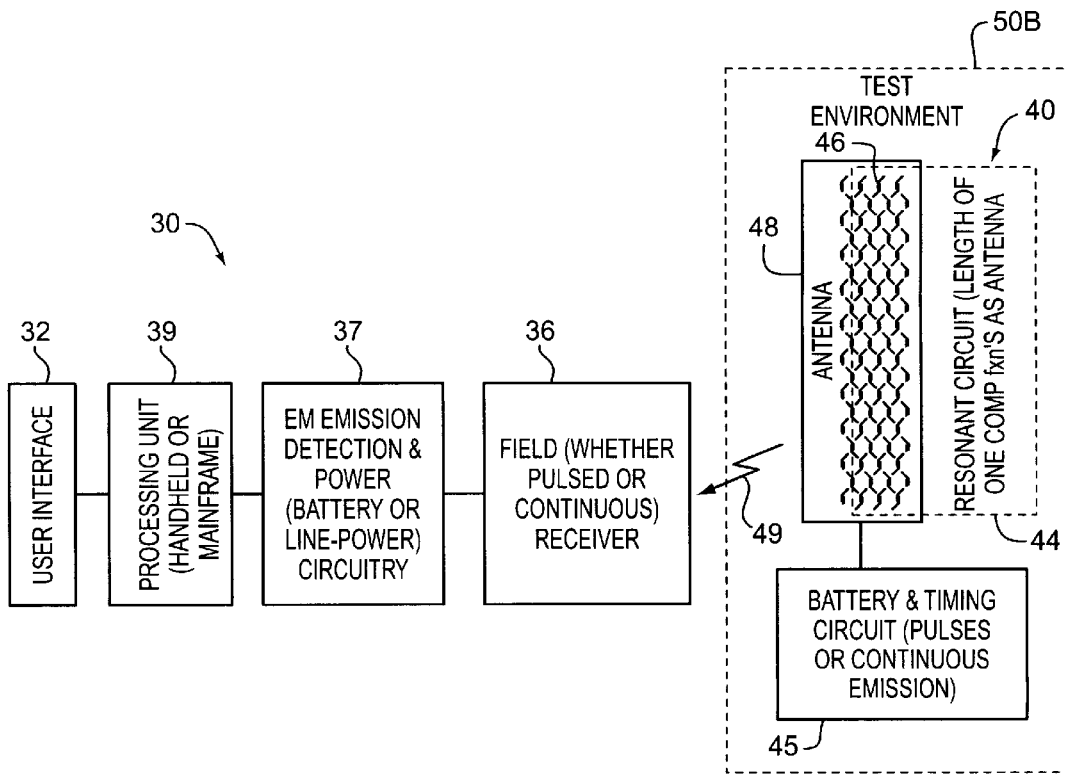

In each of the FIGS. 1A–1B, a preferred sensing apparatus 10, 30 of the invention is illustrated in schematic-block diagram form having a sensing structure (similar to those depicted in FIGS. 2A–2E) arranged for operation within an environment defined by a dashed-line boundary labeled 50A and 50B. Boundaries 50A, 50B represent a multitude of different environments of varying sizes and conditions within which the analyte in question and/or its temperature is sensed. By way of example, the sensor environment might be one encountered in a biomedical application (such as in vivo or in vitro, within or in proximity to a medical test sample, and so on). Or, the environment might be one encountered when: performing food quality/inspection (such as sealed packaging within which, or in proximity to, moisture or airborne germ(s) are monitored); monitoring of heavy metals found in groundwater, treated water, or wastewater (flowing in natural or manmade waterways, canals, wells, or pipes), and monitoring waste from manufacturing processes (whether the waste is a pollutant and is in solid-particulate, aqueous solution, or gaseous form).

The preferred analyte sensing apparatus depicted in block form at 10 in FIG. 1A includes a transmitting subassembly having a frequency generator or oscillator whose output is fed to a power amplifier (box labeled 11) which, in turn, feeds a time-varying electromagnetic field generating antenna 12 (such as a helmholtz field coil). A receiving subassembly is depicted at 18. A coil unit 16 is illustrated comprising both the field generating antenna 12 and a field receiving antenna 14; separate antennas may be used as illustrated, or a single antenna may be employed for purposes of design simplification, ease of use, and portability. Suitable shapes for the transmit/receive antennas labeled 12, 14, 36 include conductive coils, spirals, elongated wires and cables, and so on. Coil unit 16 may be handheld (especially for in-the-field use) or suitably anchored. The field generating antenna 12 establishes an alternating EM field of desired frequency and amplitude in the environment bounded by dashed line 50A. The amplitude of the field necessary to generate a predetermined signal level (sensor amplitude response) will vary depending upon system parameters such as coil size, electric characteristics of the resonant circuit, and sensitivity of receiving electronics in unit 18.

Illustrated in both FIGS. 1A–1B is a suitable receiving unit 18, 36 used to measure electromagnetic emissions (represented by arrows labeled 29b and 49) emanating from a respective sensing structure (20, 40). Suitable emission detection circuitry (represented by box 17 in FIG. 1A and box 37 in FIG. 1B) is in communication with a field/emission receiving coil (14, 36). For example, the detection circuitry (17, 37) can include a frequency spectrum analyzer programmed to "listen" over a preselected operating range of characteristic resonant frequencies, or (using a lock-in amplifier) "listen" for a particular pulse emitted at a particular characteristic resonant frequency. An inexpensive frequency mixer(s) and frequency-to-voltage converter chips can be incorporated to obtain a voltage signal suitable for electronic evaluation. The specific type of antenna used to detect emissions 29b, 49 from any one, or several, of the sensors within a boundary 50A, 50B will depend upon (among other things) the type of emission being received, the distance the emissions travel, and physical design of the receiving antenna. For example, a sensing apparatus designed for detecting electromagnetic emission considered in the low frequency range (up to about 20 MHz) must be paired with a suitable EM pick-up coil located up to a kilometer from the sensing structure; whereas, if the emissions must travel a much greater distance (several kilometers—such as that from a satellite), the equipment preferably must be capable of operation at higher frequencies (above 20 MHz to the 80 GHz range). Antennal technology for designing an EM send/pick-up antenna suitable for use, here, capable of operating up to 80 GHz is readily available.

Just prior to measuring the intensity of emissions (29*b*, 49) from a sensing structure such as 20 or 40, a pulse of sufficient duration to induce current through the resonant circuit (labeled 24, 44) can be sent (arrow 29*a*) from a transmit antenna 12 by turning on, then immediately off, the time-varying interrogation field to "listen" for an EM resonating response (arrow 29*b*) that takes place over a very short period of time (on the order of hundreds of milliseconds). Pulsed signals may alternatively be emitted from the sensing structure, itself. In either case, preferably the pulses are emitted as a short square-wave pulse (on the order of milliseconds, microseconds, nano- or femtoseconds—as short as practicable in light of any inherent physical limitations); however, linearly ramped or sinusoid pulses may be used. Note however, that it is not necessary to turn off (i.e., pulse) the time-varying interrogation field 29*a* in order to detect EM emissions 29*b* (containing desired sensing information) which originate from the sensing structure 20, 40.

Information gathered about the environment (such as those labeled 50A, 50B) by the receiving unit 18 is sent to a processing unit 19 (such as a dedicated microprocessor controlled by software components or subroutines to perform complex or simple data acquisition, processing and manipulation for an apparatus or method of the invention) which is, in turn, connected to a user interface 22 of suitable type such as a monitor screen (which may be touch-sensitive) that can display alphanumeric or waveform information, one or more light emitting diode (LED) indicators (such as a display of color-coded LEDs), automatic audio message or siren, and so on. Depending upon the nature and location of the environment being sensed, the user interface 22 may necessarily be located nearby, or several hundreds of miles from the environment (depicted within boundary 50A or 50B) and processing unit 19 to communicate via digital phone line, coaxial cable, or satellite link. Operational details, and flexibility in design of, the preferred sensing apparatus of the invention will be discussed, further, in connection with the preferred, novel method of sensing an analyte (200 in FIG. 3) to get sensing information about the analyte and/or its environment (50A, 50B in FIG. 1).

Any of several sensing structures (such as those labeled here as 20, 40 and those depicted in FIGS. 2A–2E) may be operatively arranged within boundaries 50A–50B at various orientations for independent sensing throughout boundaries 50A or 50B. Here, for purposes of drawing clarity, the sensing structures 20, 40 have been sized quite large relative to the overall size of the environment 50A, 50B in which they operate. In many applications, only one such sensing structure is needed within an environment being sensed. However, where a "package" of sensing information is desired, several separate resonant sensing structures can be ordered in an array fashion by fabricating the structures, maintaining constant relative spacing therebetween along an electrically-insulating support member. See for example FIG. 10—the sensing structures may be suitably: fixed to extend from, or atop, the member; etched within an insulating substrate member; contained within defined chambers of a support member; and so on. The overall size of this array of sensing structures is preferably on the order of several centimeters to a few micrometers, and even smaller, as the state of the art in microcircuit fabrication technology continues to become ever more-precise. As one can appreciate, a considerable range of sizes is available.

An apparatus capable of providing a package of sensing information is used, for example, where one desires to get information concerning: the presence or absence of one type of analyte (generally in the form of a fluid including aerosols, gases, solutions, etc.) within the environment, and if present, what its chemical composition is; presence or absence of a pollutant within the environment; temperature fluctuations of the environment on a real-time basis; historical temperature information; and humidity or moisture content. Each sensing structure of such an array is preferably designed and built (sized/shaped and materials) to operate over a slightly different frequency range than the other sensors within the array. This makes it easier to distinguish EM emissions received from each particular sensor of the array (i.e., to "listen for" the various sensors' emissions). In the case of using a sensing array, the receiving unit 18 preferably sweeps over a larger range of frequencies that includes at least each of the frequency sub-ranges of each individual sensing structure within the array. Sensors within an environment, whether packaged in an array or used as individual elements, are preferably sized relative to the overall volume of the environment and the size of access to the environment (which is generally small for in vivo applications). By way of example: A sensor used in vivo (within a living cell or organism) or within food packaging may need to be built on a micro-circuit scale, whereas a sensor positioned outside a smokestack or within a sealed pipe can be built on a much larger scale to facilitate ease of monitoring. Furthermore, sensor size is dependent upon sensitivity of the receiving unit 18 used to measure energy emission from the sensor. For example, a planar coil-like sensing structure fabricated with a thermally responsive structural element (see FIGS. 1A–1B at 20, 40) from which 60 kHz EM wave is emitted, can determine temperature of an environment.

Depending upon the specific use of the sensing structure, it may be important or even necessary, to more-closely control operating characteristics of individual sensing structures of the invention by superimposing a DC magnetic bias field around the area of an inductive component in the resonant circuit and/or, likewise, superimpose a DC electric field surrounding a capacitive component in the resonant circuit. The superimposing of a DC bias field in this manner, in-effect, creates a dedicated "designer-field", if you will, consisting of DC and AC field components around a respective electrical component(s) of the sensing structure to maximize its emission response (in an effort to make it more-predicable) depending upon design (size/shape and materials used) of the structure. One may also use a DC magnetic bias field in connection with an inductive component, and/or a DC electric bias field in connection with a capacitive component, as an ON-OFF switch for the sensing structure to knock its resonance out of a predetermined-expected operating range. The resonant frequency value for a sensor of given size/shape and materials can be identified by measuring successive values for emission intensity taken over an operating range of interrogation frequencies. In the event a DC bias field is superimposed nearby a component of resonant circuit (such as that at 24, 44), an identification of the sensor's resonant frequency can readily be done, to calibrate the sensor, by holding the DC bias field strength fixed and varying (sweeping over) the frequency of the AC field, or vice versa.

Figure 2A:
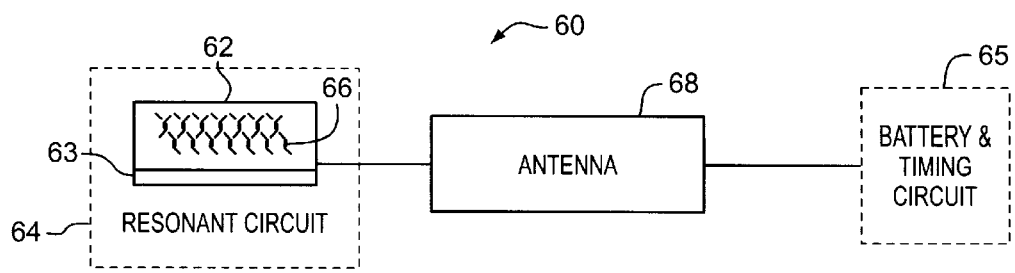
FIGS. 2A–2E diagrammatically illustrate alternative sensing structures of the invention; Here, one can better appreciate the flexibility of the invention's design and operation.
Figure 2B:
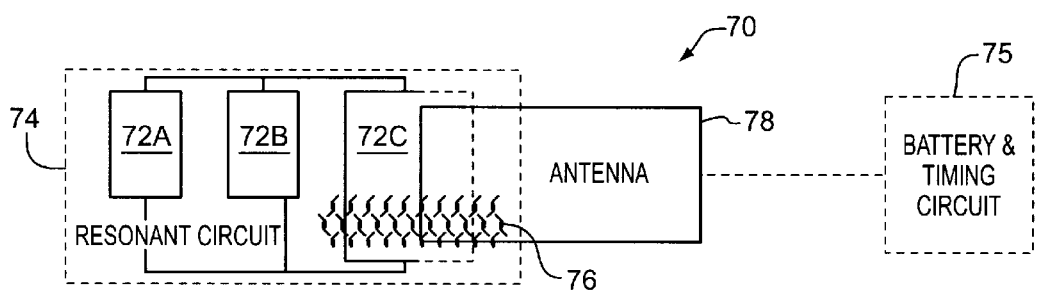
Figure 2C:
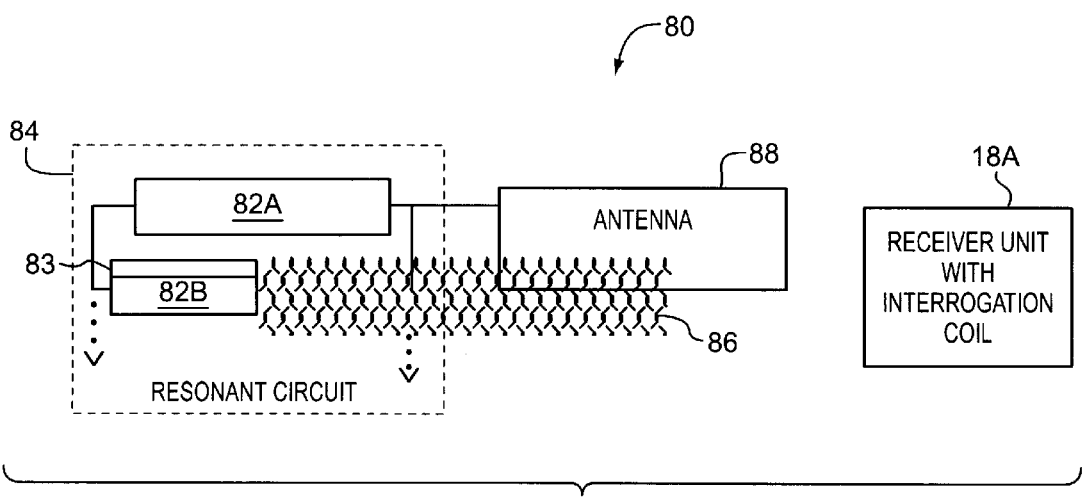

A magnetic DC bias field superimposed around an inductive component, may be generated by simply passing a DC current through a suitably-sized coil positioned an appropriate distance from the respective electrical component, or this DC bias field may be generated by other suitable means, such as to position a magnetized (activated) appropriately-sized magnetically hard material (MHM) element nearby (see FIG. 2A at 63 and FIG. 2C at 83). One useful way to provide a DC electric bias field around a sensor structure is to position an appropriately-sized ferroelectric (activated) element nearby, such as is represented in FIG. 2A at 63 and in FIG. 2C at 83, whether for use as an ON-OFF switch for the sensor, or enhance its response. Ferroelectric substances are capable of displaying ferroelectricity. They are crystalline substances such as barium-titanate, lead-zirconate titanate, potassium dihydrogen phosphate, and Rochelle salt; and are often used in ceramic capacitors, acoustic transducers, and dielectric amplifiers. Ferroelectric elements, as contemplated herein, are most-useful when positioned adjacent dielectric-based components (such as a capacitor) for activating to support external a DC electric field.

FIGS. 2A–2E diagrammatically illustrate alternative sensing structures of the invention so that one can better appreciate the flexibility of the novel design. Sensing structure 60 in FIG. 2A includes an antenna in electrical communication with a battery and timing circuit assembly (represented by block 65) and a resonant circuit 64 having at least the one component 62 shown, with a structural element 66 made of a material that selectively responds to the analyte/temperature. As mentioned, component 62 may be capacitive, inductive, or resistive in nature as long as the specific electrical component chosen, in communication with other circuitry, cause resonant circuit 64 to resonate in a manner detectable by a remote receiving unit (18, 36 in FIGS. 1A–1B). Assembly 65 is preferably powerful enough to permit emission from sensing structure 60 of a series of short pulses at predetermined intervals, of sufficient energy to be detected by an associated remote receiving unit. The component represented by block 62 has, proximately located, a ferroelectric element 63 which can be activated to affect the emission response of the sensing structure. As one can appreciate, the various components represented in schematic form in FIGS. 2A–2E are readily fabricated using known electrical component fab techniques—the sizes of which (as mentioned) will depend on the environment in which the structures 60, 70, 80, 90, 100 will operate. Fabrication techniques continue to improve for electrical components and associated circuitry used in both digital and analog environments as fab equipment becomes more sophisticated and advances are made in material compatibility. Critical, here, is the compatibility of the selectively responsive element 66 with surrounding resonant circuit 64 features, including the ability to adhere to a respective component (e.g., such as that labeled 62) and/or antenna (e.g., 68).

In FIG. 2B, resonant circuit 74 has three components 72A, 72B, 72C shown electrically connected in parallel, the values of which are chosen to create circuitry that resonates in the presence of an interrogation EM field produced by a separate coil or by power assembly 75 (whether, or not, in direct electrical communication with sensing structure 70 so that current can be directed through resonant circuit 74). The connection between the portable power assembly 75 and sensing structure 70 is shown as a dotted-line, illustrating that assembly 75 may, instead, be directly connected to a separate antenna to emit pulses therefrom to generate a suitable interrogation field that will cause the sensing structure 70 to resonate. Component 72C preferably has at least one conductive segment (such as a loop, a coil in the form of a planar spiral or of a cylindrically shaped series of loops, a straight or curvilinear shaped wire, a "flat plate", or other suitable shape), wherein at least a length of this conductive segment functions also as antenna 78. And, in the event at least a part of the structural element (shown here at 76) is bonded to this length, the selective response would cause a change in electrical characteristics of antenna 78. For example, if component 72C is designed in the form of a capacitor its conductive segment may be in the form of a generally planar coil such that it also functions as an antenna 78; this capacitor having a second conductive segment (which may also be shaped as a generally planar spiral coil, or a flat plate, etc.) between which the structural element 76 is sandwiched, see also FIG. 4B. Using component fabrication techniques known in the art, these two conductive segments are readily patterned (such as by subtractive etching) onto a laminate substrate support which may be made of many suitable polymeric, ceramic, cellulose-based, etc. materials. For example, in FIGS. 1 and 3 of U.S. Pat. No. 5,754,110 the patterned opposite sides of the security tag described therein are illustrated.

If, due to the nature of component 82A, it is desirable that component 82A not be in direct contact with structural element 86, the structure shown in FIG. 2C may be employed. This sensing structure (labeled 80) has a resonant circuit 84 with at least two components 82A and 82B, the second of which has structural element 86 adhered to it and a DC bias generating element 83 positioned nearby (or alternatively, bonded to component 82B) for use as an ON-OFF switch for the sensor, or to enhance its response. As mentioned above, the use of such an element 83 is especially desirable in the event it becomes important to either: (1) superimpose dedicated bias fields (to effect respective designer-fields) around one or more sensor structure, or (2) activate the DC bias generating element to effectively 'turn-off' any particular sensing structure, whether in an array, by causing its characteristic resonant frequency to fall outside of the arrays operating range. The added frequency response control afforded by the use of a DC bias element is especially helpful if a selected "package" (for example, see FIG. 10 at 300) of sensing information is sought from one single environment. The structural element represented at 86 in FIG. 2C extends to directly contact both component 82B of the resonant circuit 84 and antenna 88: For example, the structural element may be in the form of a thin film of selectively responsive material to which at least a substantial portion of both a conductive segment of component 82B, and of antenna 88, are adhered. Receiver unit 18A is also shown—here, it is used to generate the interrogation field that causes sensor 80 to resonate and emit EM energy back, for detection by the same unit 18A.

In the event either DC bias generating element 63 or 83 (FIGS. 2A and 2C) operates as an ON-OFF switch capable of remote activation in connection with an inductive-type component, this can be accomplished as follows: The MHM element is initially demagnetized with only a minimal stray magnetic field so as not to interfere with operation of the sensing structure (60, 80). To turn sensor 60 or 80 OFF, the MHM element 63, 83 can be exposed to a large DC electromagnetic field, such as that emitted by a magnet, which magnetizes/activates the MHM so that it supports a large external stray magnetic field. The MHM layer may be designed so that the stray field of an activated MHM is either larger than the interrogating EM field (whereby the sensor 60 or 80 effectively no longer responds to the interrogation field), or the activated MHM can act to bias the respective component 62, 82B such that the resonant frequency of sensor 60, 80 is no longer within operating range of a receiving unit (such as 18A in FIG. 2C). The sensor 60, 80 can be remotely reactivated by demagnetizing the MHM element 63, 83 by exposing it to a time-varying, gradually decreasing magnetic field the initial amplitude of which is greater than the MHM's coercive force. Suitable magnetically hard materials for switch elements include ferromagnetic metal alloys and their oxides, made to support large external fields.

Figure 2D:
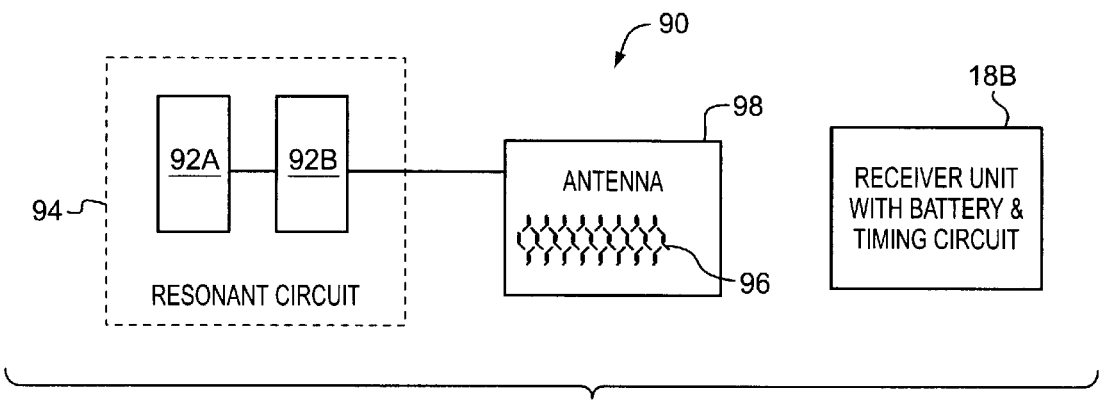
Figure 2E:
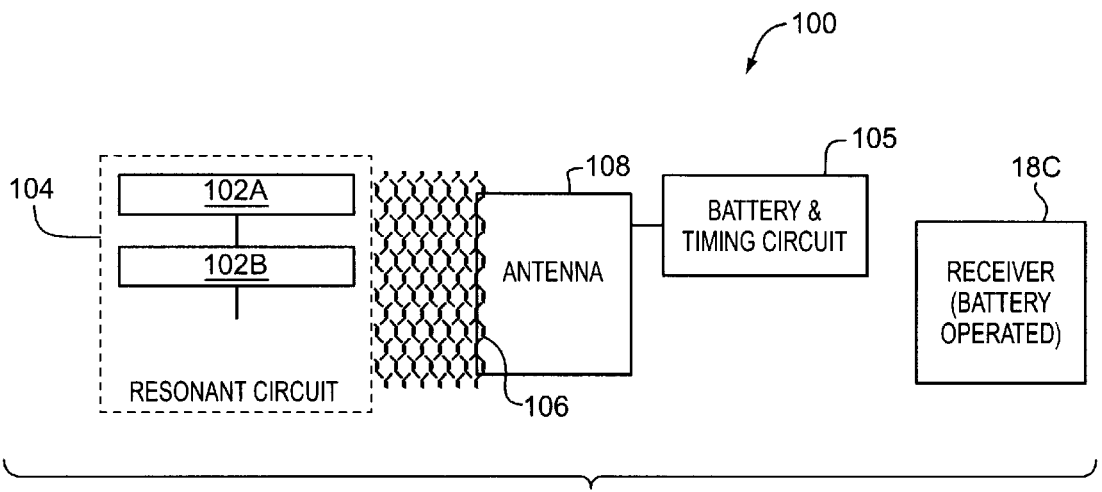

The flexibility of design is further illustrated in FIGS. 2D and 2E. Resonant circuit 94 has two blocks labeled 92A, 92B representing components which may (as discussed above in connection with FIG. 2B) be capacitive, inductive, or resistive in nature as long as the electrical components used, in communication with other circuitry, cause resonant circuit 94 to resonate in a manner detectable by a remote receiving unit such as that labeled 18B. In FIG. 2D, one can see that the feature comprising the selectively responsive element 96 is antenna 98. As discussed herein, many suitable responsive materials may be used. Antenna 98 may be patterned onto a substrate support; alternatively, all or a portion of the antenna 98 may be coated with a thin film of the selectively responsive material, and so on. It is critical that the structural element 96 be compatible with the antenna structure 98 (for example, see FIGS. 6A–6D) such that the element 96 can interact with the analyte or respond to temperature changes, thus, affecting EM emissions from sensor 90.

Turning to FIG. 2E, one can see that the sensing structure 100 is comprised of resonant circuit 104 (having components 102A, 102B connected in parallel) communicates with an antenna 108; structural element 106 being located between resonant circuit 104 and antenna 108. Structural element, by way of example as represented at 106, may be in the form of a substrate base-support having a thin-film of carbon nano-tubes that selectively respond to (by absorption) hydrogen gas ($H_2$) as it passes over. In this embodiment, a portable power assembly 105 having a battery and timing circuit is directly hardwired as part of the sensing structure 100 allowing it to resonate for detection by a receiver such as that labeled 18C. Assembly 105 can be employed to emit short pulses, or an extended EM signal wave, as desired from antenna 108.

The material out of which the structural element (26, 46, 66, 76, 86, 96, 106) is made is preferably chosen for a desired selective response to an environmental condition (including, an analyte's chemical and/or thermal responsiveness). There are many suitable materials. The structural element, for example, may be made of a chemically receptive polymer that has microspheres (or, microbeads) capable of absorbing particulate matter (e.g., a sub-atomic particle such as a proton) in the analyte. One implementation of this is to prepare monolayers of lightly crosslinked derivatized polystryene microspheres having diameters on the order of 0.3 to 0.5 micometers. This is done by dispersion polymerization of vinylbenzyl chloride with ca. 2 mole-% divinylbenzene as the crosslinker. The chloromethyl group is aminated to introduce an amine group. This polymer swells upon protonation at low pH: Its microspheres swell individually, tending to minimize mechanical stresses on the polymer, thus, tending to reduce cracking of the layer and delamination from the conductive segments that make up the component (62, 72C, 82B) and/or antenna (98, 108). This implementation may be used for sensing a pH level of the analyte.

Another suitable material for the responsive structural element (26, 46, 66, 76, 86, 96, 106) is the pH sensitive chemical transduction spacer layer made of a polyacrylate polymer, such as a lightly crosslinked 2-(dimethylamino) ethyl methacrylate (DMAEMA), which is described in the scientific article A Remotely Interrogatable Magnetochemical pH Sensor, IEEE TRANSACTIONS ON MAGNETICS, VOL. 33, No. 5, SEPTEMBER 1997 (cited above), developed in collaboration with the applicant hereof. Polyacrylate polymers are known to be hydophilic and, therefore, swell in water. Thus, the polymer network is permeable to aqueous analytes. This article identified that thin films of polystyrene will swell in the presence of toluene and that polyhydroxyethyl methacrylate swells as a function of analyte moisture content (humidity). Any of these materials are suitable, here.

Hydrogels are crosslinked hydrophilic polymers which swell upon contact with moisture by reacting to the electrostatic forces of sub-atomic particles. Examples of synthetic hydrogels include: contact lenses and polymerized hydroxyethylmethacrylate (HEMA). N. F. Sheppard. Jr. et al. Microfabricated conductimetric pH sensor, Sensors and Actuators B vol. 28 (1995) 95–102 used a copolymerized HEMA with 2-(dimethylaminoethyl methacrylate (DMAEMA), which introduces an amine group onto the polymer backbone, in their conductimetric pH sensor. Here, a lightly crosslinked polyHEMA-co-DMAEMA could be used since it swells at low pH when the amine group is protonated.

A chemically receptive porous structural element (26, 46, 66, 76, 86, 96, 106) into which the analyte can diffuse may be advantageous (such as by the transport of mass, in the form of discrete atoms, through the lattice of a crystalline solid); or one might incorporate an outer diffusion barrier (a porous barrier through which gaseous mixtures are passed for enrichment of the lighter-molecular-weight constituent of the diffusate). It may be desirable, depending upon desired EM emission, to adhere the responsive structural element over one or more small areas of the resonant circuit component (such as that shown in FIGS. 2A–C at 62, 72C, 82B) or the antenna (shown in FIGS. 2D–2E at 88, 98, 108). Another material option for the structural element is a sorbant polymer film capable of vapor diffusion, selected from a group of sorbant polymer film materials identified in J. Grate, M. Abraham, Solubility interactions and the design of chemically selective sorbent coatings for chemical sensors and arrays, Sensors and Actuators B, vol. 3 (1991) 85–111, to include at least: poly(isobutylene), ethylenepropylene rubber, poly(isoprene), and poly(butadiene).

Other materials with chemical response mechanisms that make them suitable for use as the responsive structural element of the instant invention include the following: (1) a hydrogel having boronate-containing polymer complexes that swell due to diffusion of ion species upon chemical responsiveness when in contact with glucose to sense glucose (blood sugar) concentration changes (as identified by A. Kikuchi et al., Glucose-Sensing Electrode Coated with Polymer Complex Gel Containing Phenyl-boronic Acid, Anal. Chem., vol. 68, pp.823–828, 1996; (2) a material capable of loss of particulate matter (such as a sub-atomic particle/proton) when interacting with the analyte; (3) a polymer capable of molecular interaction with, by-way-of absorption, the analyte to change the mass of the layer; and (4) zeolite (a clay-like structure that exhibits the behavior of a molecular sieve or filter—a crystalline compound), which "filters" carbon-rich gases flowing over the layer, causing a change in mass of the layer. The outer surface may also be that of a material (such as a polymer) that is thermally responsive to the environment within which the sensor has been positioned. One suitable material is a thermally-sensitive elastomer (or the "thermosensitive rubbery polymer" described by Y. Nagasaki et al. in the scientific article New Thermosensitive Rubbery Polymers. Synthesis of Poly (siloxyethylene glycol), Macromolecules 1996, 29, 5859–5863) which responds by thermo-chemical reaction with the intent of causing material swelling and a corresponding mass change in the layer, and/or change in material stiffness of the layer. Thermochemical reactions include those chemical reactions accompanied by a heat change (whether exothermic or endothermic), and perhaps also a change in state.

A novel sensing apparatus of the invention that senses temperature may incorporate a sensor (such as those represented at 20, 40, 60, 70, 80, 90, 100 in FIGS. 1A–1B and 2A–2E) with a thermally responsive structural element substrate-layer having a coefficient of thermal expansion (CTE) causing it to readily change in response to a change in temperature. By definition, the coefficient of thermal expansion of a material in solid, liquid, or gas phase is defined as: the increment in volume of a unit volume of the material for a rise of 1-degree temperature when the material is held at constant pressure. An associated resonant circuit component(s) such as those depicted in FIGS. 2A–C at 62, 72C, and 82B, or corresponding antenna in FIGS. 2D–2E at 88, 98, and 108, can be constructed by adhering (bonding/etching/screen-printing or otherwise patterning) conductive segment(s) atop one or both sides of a structural element substrate-support capable of changing dimension(s), by expanding for example, in response to a temperature change. Likewise, a component (whether resistive, inductive, or capacitive in nature), or a sensor antenna, may be constructed with a thermally responsive structural element in much the same manner it is constructed with a chemically responsive structural element. By way of example only, antimonial lead has a CTE value of about $28\times10^{-6}$/degree kelvin composed of 96% lead (Pb) and 4% antimony (Sb), and Zinc has a CTE value of about $31\times10^{-6}$/degree kelvin, may either be sputtered, evaporated, or chemically deposited, or otherwise adhered using known techniques onto a conductive segment made of an alloy which has a lower CTE. In this example, for a given series of unit variations in temperature (degree kelvin), the thermally responsive element will change size at a "faster rate" in response to the rise or fall in temperature than will an associated conductive segment which will essentially remain unchanged by the temperature variation.

If chemically sensing an analyte (its presence, concentration, composition, and so on) it is preferable to choose a selectively responsive material that remains relatively stable, i.e., its material properties do not change a significant amount over a wide range of operating temperatures. On the other hand, if sensing temperature with a sensing structure that has a thermally responsive structural element (such as a thermally responsive polymeric layer), it is preferable to choose a material capable of significant change with fluctuations in temperature to change the sensing structure's characteristic resonant frequency.

As is known, electric and magnetic fields are fundamentally fields of force that originate from electric charges. Whether a force field may be termed electric, magnetic, or electromagnetic hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motions, on the other hand, produce both time-varying electric and magnetic fields termed electromagnetic fields. See the textbook, *Engineering Electromagnetic Fields and Waves*, Carl T. A. Johnk, John Wiley & Sons, 2$^{nd}$ Edition (1988). One well known use of these principles of electromagnetism is the transformer: An assembly having a ferromagnetic core around which a primary coil carrying a time-varying current is wound and a secondary coil is wound (into which an associated current is induced as a result of the time-varying magnetic field induced in the ferromagnetic core).

Jumping ahead to FIG. 4A, the resonant circuit sensing structure pictured therein (as also illustrated in FIG. 1A at 20) includes an spiral antenna 28, the ends of which are terminated in a parallel connected capacitor(22A)-inductor (22B) pair having, together, a characteristic resonant frequency $f_0$ according following mathematical relationships.

$$f_0 = \frac{1}{2\pi\sqrt{LC}} \qquad [1]$$

where L is the inductance value of inductor 22B and C is the capacitance value for capacitor 22A. In response to a variable, frequency modulated EM interrogation field, the antenna 28 will self-resonate $f_1$, which is a function of both $f_0$ and the characteristic resonant frequency of the antenna as determined by its physical dimensions. As diagramed, the antenna(28)-resonant circuit(24) assembly will most-strongly reflect incident energy at its characteristic frequency $f_0$. In connection with a selective response of either the capacitor 22A, inductor 22B, and/or antenna 28, acting alone or in some combination, the sensing structure diagramed will emit a "reflecting" characteristic resonant frequency $f_1$ different from (nevertheless, related to) its resonant frequency $f_0$ prior to any responsiveness.

Additional important relationships to help predict sensing structure behavior are as follows. For a capacitor having two conductive segments, each shaped as a (large) plate:

$$C = \epsilon\frac{A}{d} \qquad [2]$$

where C is capacitance of the component, $\in$ is the dielectric constant of the dielectric material positioned between the two conductive plates, A represents the area of each plate (sized approximately the same), and d is the distance between the two conductive plates. Dielectric constant, $\in$, is also considered the relative permittivity specific to a material:

$$\in = \in_{0(permitivity\ in\ free\ space)} * \text{material specific value} \qquad [3]$$

where $\in_0$ represents permittivity in free space (a constant appearing in Coulomb's law having a value of 1 in centimeter-gram-second electrostatic units, and of $8.854\times 10^{-12}$ farad/meter in meter-kilogram-second units).

One can readily appreciate that if the dielectric material is chosen to selective respond to a change in its environment (the analyte, for example), thus causing the value for $\in$ to change, the capacitance value for the component will change. For a toroid that encloses an area, $A=\pi r^2$, having n turns and current I running through it, its inductance L is given as:

$$L = \frac{\rho n^2 A}{2\pi r} \qquad [4]$$

where ρ is its magnetic permeability and r is the inner radius of the toroid. Once again, an inductor fabricated with a structural element of a material that selectively responds to a change in its environment (the analyte, for example), thus causing the value for ρ to change, the inductance of the component will likewise change.

By way of example only, a planar capacitor (such as that labeled 22A in FIG. 4A) may be suitably constructed by placing parallel metal strips a small distance apart upon a polymer substrate element that either, selectively swells or shrinks in response to the presence of an analyte-solution without changing dielectric constant, or selectively change dielectric constant in response to coming into contact with the analyte-solution without changing physical dimensions of the capacitor. By way of further example, a planar inductor may be suitably constructed of several thin ferromagnetic strips, or loops, etc. oriented adjacent one another in a parallel manner (so as not to cross paths) may be etched, screen-printed, or otherwise patterned on a polymer substrate element (which may also have particulate ferromagnetic elements embedded therein). The strips have an initial inter-strip magnetostatic coupling. When this polymer substrate element interacts with the analyte (shrinks, swells, etc.) the spacing between the strips (affecting the inter-strip mangetostatic coupling) and/or spacing between particulate ferromagnetic elements changes causing a net change in the inductor component's magnetic permeability. Consistent with relationship [4] above, a change in magnetic permeability changes the inductance value of the component.

Turning back to FIG. 3: Operation, and flexibility in design, of a preferred sensing apparatus having features diagramed in schematic-block form in FIGS. 1A–1B, 2A–2E, can be better appreciated in connection with the preferred, novel method of sensing labeled at 200 in FIG. 3. Here, rather than working at a single fixed interrogation frequency and checking for amplitude like known resonant anti-theft EAS markers do, the novel sensing apparatus and method of the invention look at the frequency response of the sensor for sensing information about an analyte, including temperature of the environment in which the sensing structure has been placed. The new sensing apparatus and method of the invention provide sensing information about environmental conditions in which a sensing structure has been operatively arranged, by measuring intensity of an electromagnetic (EM), or other such emission from the sensing structure, once a selective response of a structural element takes place—the sensing structure being either a part of at least one of the components in a resonant circuit, and/or a part of the sensor's antenna. In effect, and as contemplated herein, the interrogation field acts as a power source for the sensing apparatus of the invention (regardless of where the interrogation field originates) causing the sensing structure(s) to operate as a passive element(s) with no mechanical linkages/physical connections (to the receiving unit) subject to wear. Thus, a sensor structure's product life is generally limited by physical properties (e.g., strength/durability) of the materials used, the responsiveness of the structural element(s), and the type of environment within which the sensing structure(s) operates (e.g., whether caustic or under extreme temperature fluctuations, or whether additional static or fluid dynamic forces will act on the sensor, etc).

It may be desirable (and, in some cases necessary) to cap or cover a selectively responsive structural element with a protective or bio-compatible coating, such as titanium or polyethylene glycol, especially in the event the sensor is placed within an environment (FIGS. 1A–1B 50A–50B) that is chemically harsh or within a human body (such as the stomach). It is preferred that the selectively responsive element not be completely sealed by such a coating so as not to degrade its responsiveness to the analyte or its temperature.

Figure 3:
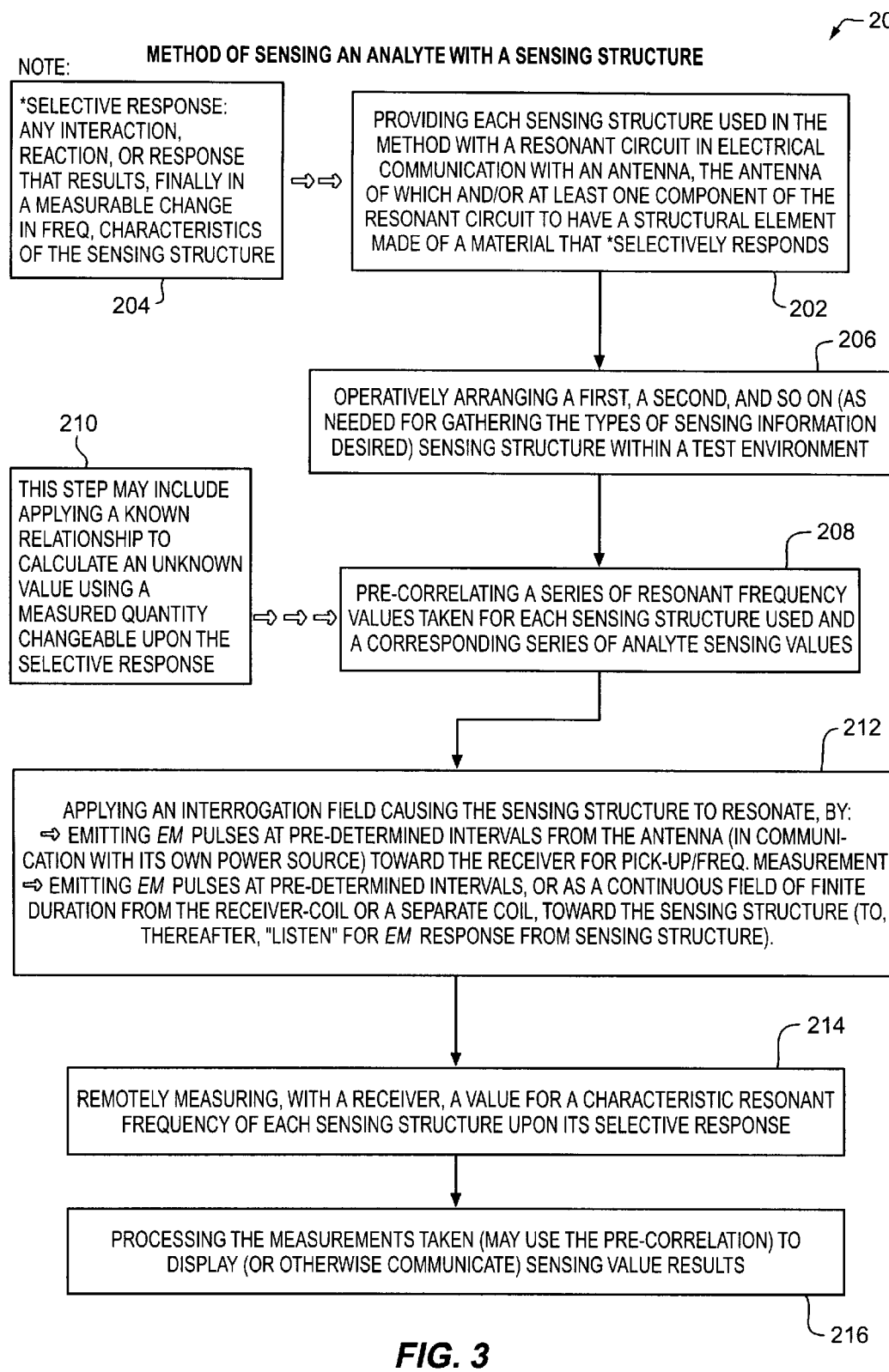
FIG. 3 is a flow diagram detailing preferred steps of a method of sensing an analyte as further described herein.
Figure 6A:
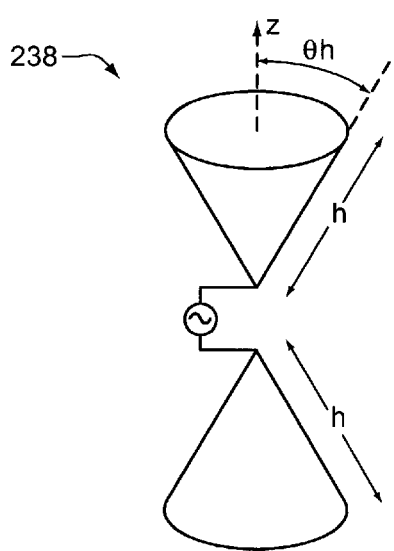
FIGS. 6A–6D diagrammatically illustrate alternative antennas (biconical antenna, capacitor-plate antenna, spiral antenna, and planar equiangular spiral antenna) any one of which, in addition to other known antenna designs, may be incorporated in a sensing structure and/or the transmit/receiving unit of the invention.
Figure 6B:
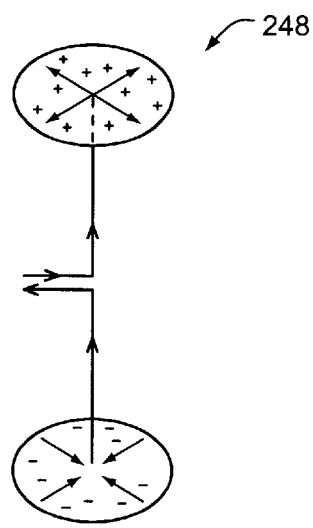
Figure 6C:
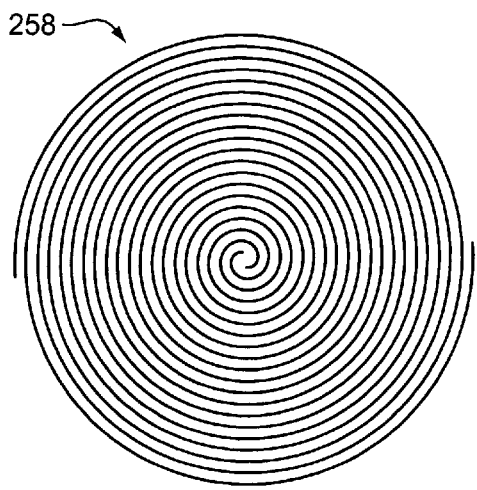
Figure 6D:
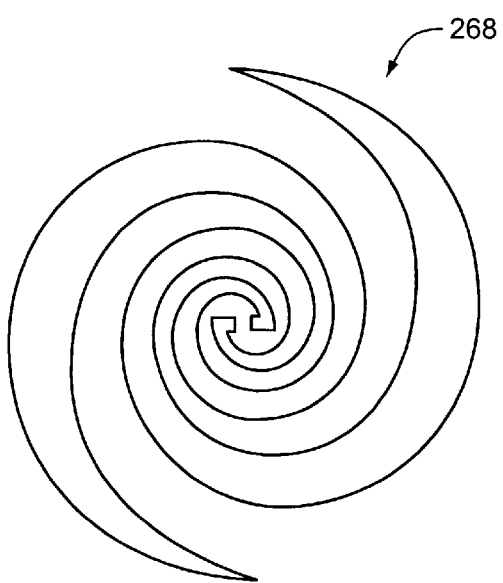
Figure 10:
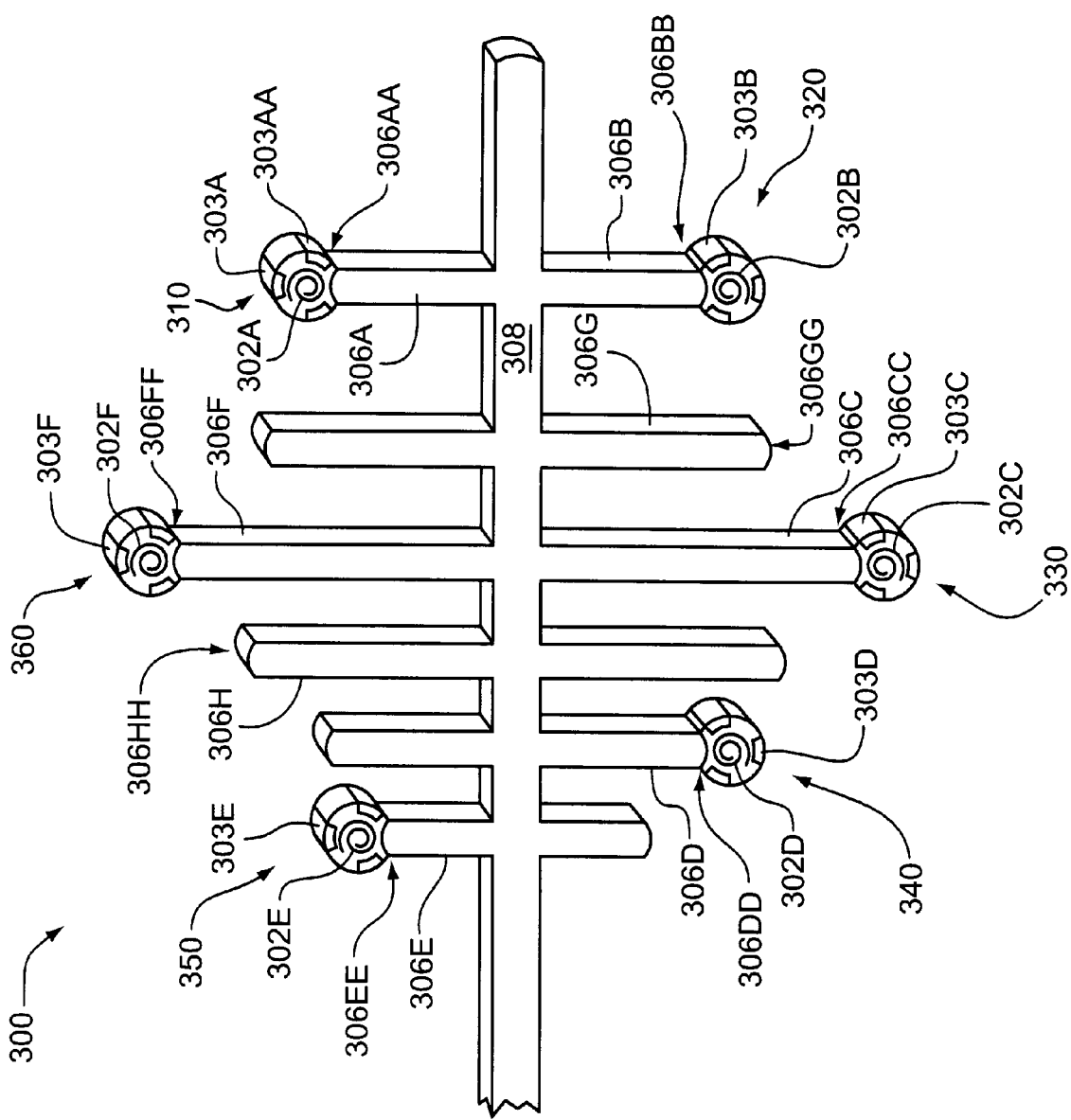
FIG. 10 represents a sensing apparatus 300 capable of providing a package of sensing information, due to the inclusion of several resonant circuit sensing structures interconnected by a structural backbone.

The top box 202 of the preferred method of sensing 200 in FIG. 3 explains that each sensing structure used (whether alone or in an array of structures such as is shown in FIG. 10) has been, first, fabricated using known techniques to have both a resonant circuit in electrical communication with an antenna. As further illustrated in FIGS. 2A–2E, at least one component of the resonant circuit and/or the antenna of the sensing structure, has a structural element made of a material that selectively responds. NOTE 204—this selective responsiveness can be by way of an interaction, reaction, or other response that results, at some point, in a measurable change in frequency characteristics of the sensing structure. Next (box 206), as many sensing structures as are needed to gather the type(s) of sensing information about the environment/analyte that is desired, are operatively arranged within a test environment. One may choose to use only one sensing structure (as illustrated in FIGS. 1A–1B) or an array of sensing structures (FIG. 10). The box labeled 208 describes a step which can be performed, for efficiency, early in the process to calibrate the sensing structure as fabricated: Making a pre-correlation of a series of resonant frequency values taken for each sensing structure used with a corresponding series of analyte sensing values. NOTE 210 further explains that this step may include the application of a known mathematical relationship to calculate an unknown value using a measured quantity changeable upon the selective response—this is preferably done with a computer processor once the wave emissions have been measured by a remote receiving unit. In order to cause the resonant circuit/antenna assembly to resonate (box 212), an interrogation field must be applied by suitable means such as: Emitting EM pulses at pre-determined intervals, or as a continuous field of finite duration, from the antenna (in communication with its own power source) toward the receiver for pick-up/frequency measurement; or emitting EM pulses at pre-determined intervals, or as a continuous field of finite duration from the receiver-antenna or a separate pick-up antenna, toward the sensing structure (and then "listen" for EM response from sensing structure). Next (box 214) is the step of remotely measuring, with a receiver, a value for a characteristic resonant frequency of each sensing measurements taken (as stated above, may use the pre-correlation) to display (or otherwise communicate) sensing value results.

As mentioned above, the receiver can include a pick-up antenna (which can be a coil-type antenna) capable of measuring a plurality of successive values for electromagnetic emission intensity of the sensing structure taken over an operating range of successive interrogation frequencies; this operating range to include the characteristic resonant frequency value of the sensing structure. The resonant frequency value detected will correspond to the relative maximum of the plurality of successive values for electromagnetic emission intensity measured. The unique design of the sensing structures described herein allow them to operate along the lines of a frequency modulated (FM) radio which, in contrast to amplitude modulated (AM) radio, is generally less sensitive to surrounding noise or signal fading. The receiver's pick-up coil/antenna can be wired in communication with a frequency analyzer (see, also, FIG. 1A).

As indicted, the component(s) used in the invention such as those depicted at 62, 72A–C, 82A–B, 92A–B, 102A–B in FIGS. 2A–2E of respective resonant circuitry 64, 74, 84, 94, 104, and corresponding antennae 68, 78, 88, 98, 198 may be of a myriad of shapes and sizes and suitably fabricated using known circuit fab techniques (whether made on a microcircuit level, using photo-lithographic or screen-printing techniques, or on a macroscopic analog-device scale). Preferably, at least one of the components of the resonant circuit is fabricated of a conductive segment (of many suitable shapes and sizes). Additionally, at least a length of this conductive segment may be used to function, also, as an antenna for the sensing structure. Furthermore, in the event at least a part of the structural element is bonded to this length, the selective response would likewise cause a change in electrical characteristics of the antenna. The simple structure shown in FIG. 4B represents a capacitor having electrically-isolated first and second conductive segments (22A' and 22B')—these segments may be relatively planar elongated segments, flat-plates, looped (whether concentric looped shapes or loops on opposite sides of a dielectric), and so on. Between segments 22A' and 22B' is at least a portion of the structural element, here labeled 26A; the two conductive segments are preferably bonded/adhered to the structural element 26A. In the event the first conductive segment is in the shape of a relatively planar spiral, it can also function as an inductor for the resonant circuit. The current state of microcircuit technology allows for ready fabrication of these types of components and antennae.

By way of example only, the graphical representation 220 in FIG. 5 includes results of EM emission data taken for the sensing structure shown in FIG. 4A used to sense pH of an analyte. A sensing structure was fabricated with a spiral antenna made of 16 gauge wire approximately 30 cm in total length, wound in a 5.0 cm radius arc and adhered to a glass (ceramic) disk. At the center of the disk a capacitor was constructed by adhering electrically insulated, parallel oriented aluminum strips, 20 microns thick by 1.8 cm in length by 4.0 mm (vertical height out of disk basal plane), to a 120 micron thick polymer thin film with $\in_r \approx 8$. Using equation [2] C≈30 pF. The inductor consisted of 50 turns of 40 gauge wire wrapped around a 6 mm diameter air core that was 2 mm deep, for a nominal inductance value of 40 $\mu$H. The measured resonant frequency of the resonant sensing structure in its initial state was 1023 MHz. This was measured by placing the sensing structure within an RF field generated by connecting the output port of an HP 8753D network analyzer programmed to sweep from 900 MHz to 1100 MHz, to an Atlanta Scientific Biconical (transmitting) antenna. The receiver port (R) of the network analyzer was connected to an identical biconical antenna used as a receiver antenna. This graphical representation 220 correlates resonant frequency of a sensing structure as a function of pH. Here, this sensor was first immersed in buffered 4.0 pH solution for 10 minutes, measured, then allowed to dry at room temperature for one hour. The sensor was then placed in buffered 10.0 solution for 10 minutes and its frequency response measured, again.

FIGS. 6A–6D illustrate, for reference, several known useful antenna structures suitable for use in the invention: A finite biconical broadband antenna 238; a capacitor-plate antenna 248 (the arrows on the antenna indicate the direction of current and the charges on the two plates are shown for reference); an archimedean spiral broadband antenna 258; and a planar-equiangular spiral antenna 268 (self-complementary case with δ=90°).

Figure 7:
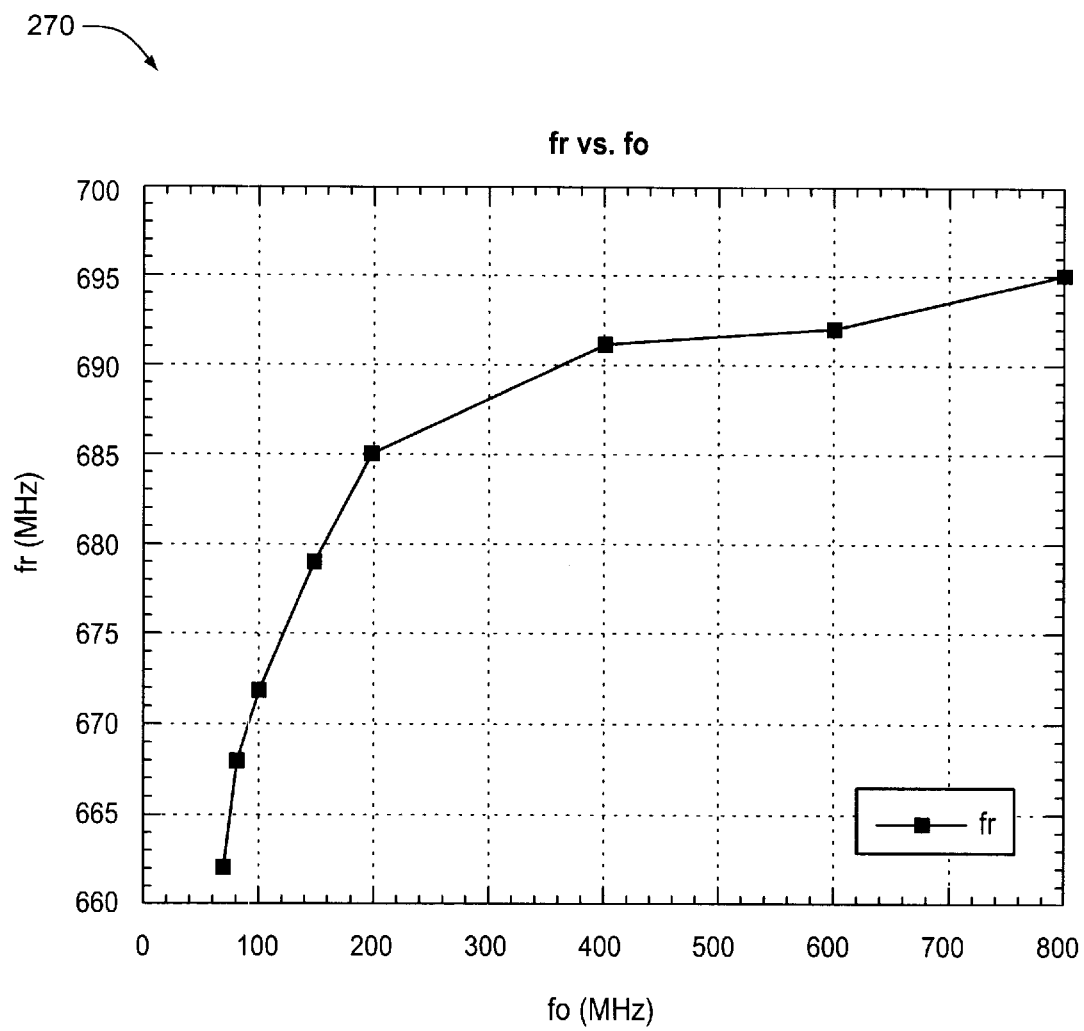
FIGS. 7–9 are graphical representations made from a computer simulation performed using a sensing structure such as the one shown with an LC-resonant circuit in FIG. 4A.
Figure 8:
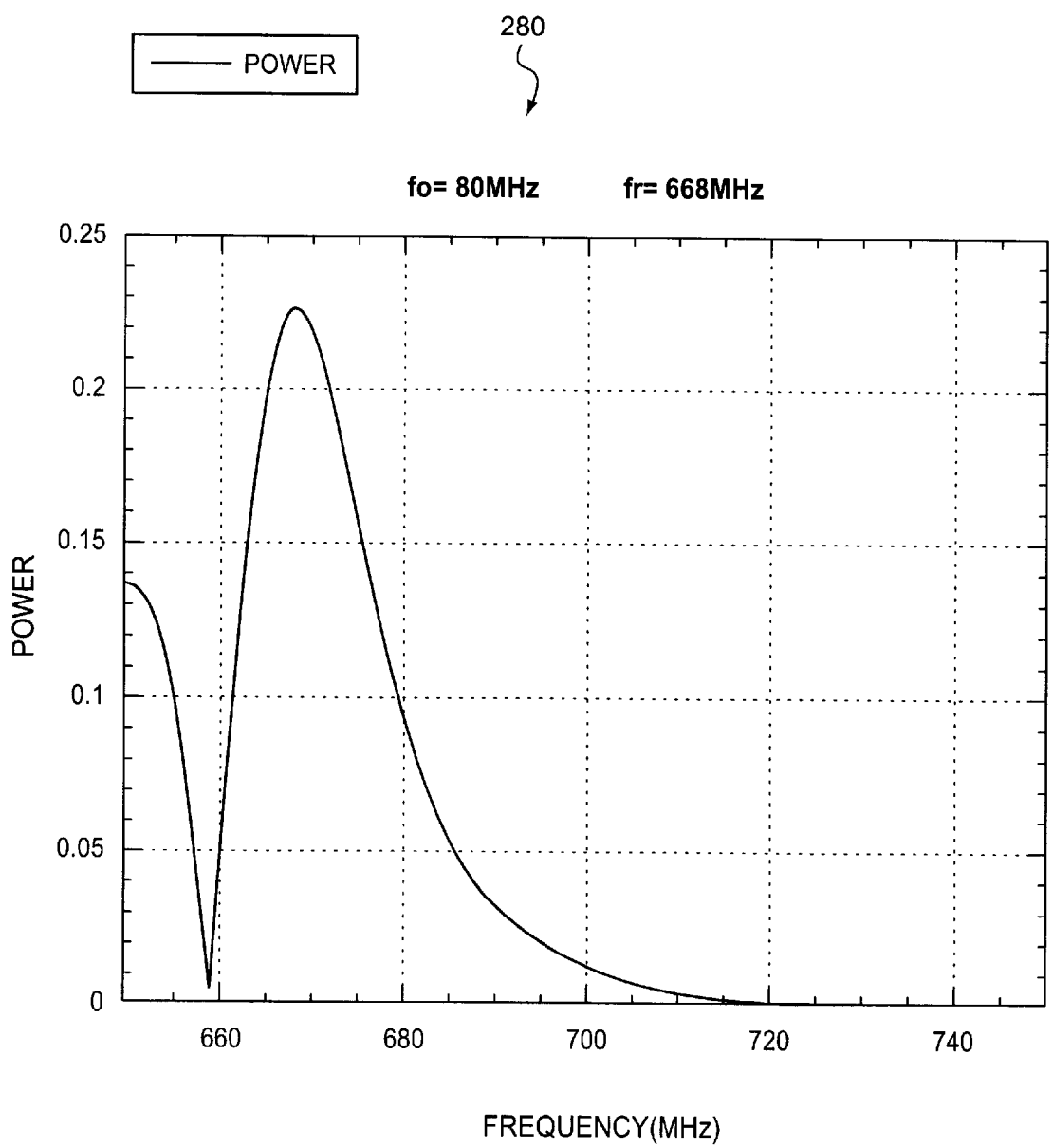
Figure 9:
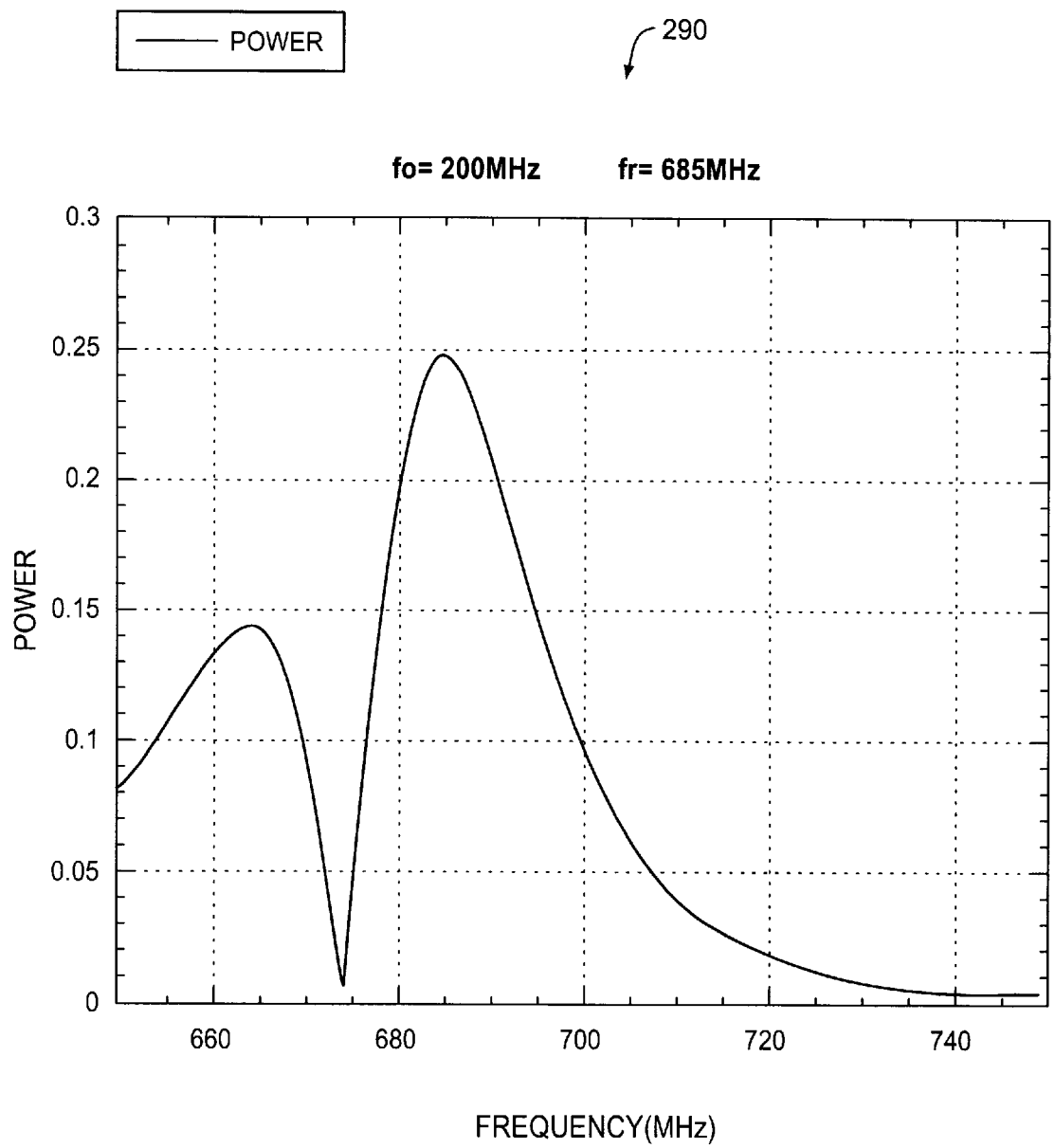

FIGS. 7–9 are graphical representations made from a computer simulation performed using a sensing structure such as the one shown with an LC-resonant circuit inG. 4A. FIG. 7 is a plot of $f_r$ resonant frequency sensing structure behaving as a reflector) vs. $f_0$ (frequency of the resonant LC circuit, measured at its terminals); and FIGS. 8 and 9 are frequency spectrum graphs for the sensing structure illustrating emission intensity peaks for the computer simulated sensing structure at $f_r$=668 MHz and at $f_r$=685 MHz (interrogation frequency values are shown along the x-axis in both graphs). n one a series of interrogation frequencies taken in 10 kHz intervals to measure a corresponding series of emissions from a sensor 1 cm×2 cm×20 microns thick sensed a 0.5 mg mass change at 60 kHz.

Turning to FIG. 10, as mentioned above, in the event a "package" of different types of sensing information about one environment is sought, more than one sensor may be maintained in an ordered array, for example, by being organized to extend along or contained within chambers of a support member. Each sensing structure 310, 320, 330, 340, 350, 360 is fixed at the end of respectively-labeled elongated fingers 306A, 306B, 306C, 306D, 306E, 306F extending from generally-insulating backbone member 308. Elongated fingers 306G, 306H have ends 306GG, 306HH to which MHM (or other suitable ferro-electric) elements can be secured for operation as ON-OFF switches or for generating designer DC bias fields for neighboring structural elements 306BB and 306FF, respectively. Each sensing structure, by way of example here, includes a spiral antenna 302A–302F with components labeled 303A–303F therearound each of which may be selectively responsive, itself, to react to environmental conditions. The component-elements 303A–303F (which may be capacitive, inductive, or resistive in nature) have been built into or adhered to structural supports labeled 306AA, 306BB, 306CC, 306DD, 306EE, 306FF each of which (also, or instead of the components) may be made of a material that selectively responds to provide sensing information about the environment in which the array 300 is arranged. Each sensing structure within array 300, preferably has a distinct operating range, allowing a receiver to distinguish emissions received from each separate sensor 310, 320, 330, 340, 350, 360.

If more information about an environment is desired, additional steps to the method 200 in FIG. 3 include: measuring a second plurality of successive values for emission intensity of a second sensor with a receiver (such as depicted in FIGS. 1A–2A and FIGS. 2C–2E) operating over a second range of successive interrogation frequencies to identify a resonant frequency value for the second sensor, and pre-correlating a second series of resonant frequency values taken for the second sensor and a corresponding second series of sensing values for this second sensor. The same, or an additional, receiver may be used to measure emission from the second sensor.

While certain representative embodiments and details have been shown for the purpose of illustrating the invention, those skilled in the art will readily appreciate that various modifications may be made to the invention without departing from the novel teachings or scope of this invention. Accordingly, all such modifications are intended to be included within the scope of this invention as defined in the following claims. Although the commonly employed preamble phrase "comprising the steps of" has been used herein in the method claims, the Applicant in no way intends to invoke Section 112 ¶6. Furthermore, in the claims, any means-plus-function clauses used (or in some way later determined to be present), are intended to cover the structures described herein as performing the recited function and not only structural equivalents but also equivalent structures.

What is claimed is:

1. A resonant sensing apparatus for operative arrangement within a test environment to which an interrogation electromagnetic field is applied to sense an analyte, comprising:

a sensing structure comprising an antenna in electrical communication with a resonant circuit having a capacitive component and an inductive component comprising a plurality of conductive windings, both of which are on a first side of a structural element made of a material that selectively responds to the analyte, said sensing structure operable to resonate at a characteristic resonant frequency in the presence of the interrogation electromagnetic field and the analyte;

said structural element comprises a plurality of particle-sized ferromagnetic elements embedded within said material;

a remote receiver for measurement of a plurality of values for electromagnetic emission intensity of said sensing structure to identify said characteristic resonant frequency;

said plurality of values for electromagnetic emission intensity comprise a plurality of successive values taken over an operating range of successive interrogation frequencies, and said interrogation electromagnetic field is so applied by generating a pulse of electromagnetic energy emitted just prior to each said measurement taken of said successive value; and wherein said antenna is a biconical antenna coupled to an electro-chemical cell and a timing circuit, said pulses being emitted from said antenna at pre-determined intervals for said remote measurement thereof by said receiver; said plurality of conductive windings are patterned onto said first side; and said corresponding series of analyte sensing values comprises analyte pH level values.

2. A resonant sensing apparatus for operative arrangement within a test environment to sense an analyte, comprising:

a sensing structure comprising an antenna in electrical communication with a resonant circuit at least one component of which has a structural element made of a material that selectively responds to the analyte, said antenna coupled to an electro-chemical cell and a timing circuit to emit a plurality of pulses of electromagnetic energy over an operating range of interrogation frequencies at a predetermined interval;

a remote receiver for measurement of said plurality of pulses to identify a characteristic resonant frequency for said sensing structure in the presence of the analyte; and a pre-correlation made between a series of resonant frequency values taken for said sensing structure and a corresponding series of analyte sensing values is used for the sensing.

3. The apparatus of claim 2 wherein said at least one component comprises a conductive segment, at least a length of which functions as said antenna, said at least one component to have at least a part of said structural element bonded thereto by coating such that said selective response causes a change in electrical characteristics thereof.

4. The apparatus of claim 2 wherein said at least one component has a capacitance value and comprises relatively planar first and second concentric conductive loop segments adhered to a surface of a first side of said structural element, and said selective response comprises an interaction with the analyte resulting in a change in material stiffness of said structural element.

5. A resonant sensing apparatus for sensing an analyte, comprising:

a sensing structure operatively arranged within a test environment to which an interrogation electromagnetic field is applied, said sensing structure comprising a resonant circuit having first and second components, each of which comprises a conductive segment bonded to a first surface of a structural element made of a material that selectively responds to the analyte in a manner that changes the frequency characteristics of said resonant circuit;

said sensing structure operable to resonate at a characteristic resonant frequency in the presence of the interrogation electromagnetic field and the analyte; and a remote receiver for measurement of a plurality of successive values for electromagnetic emission intensity of said sensing structure taken over an operating range of frequencies that includes a value for said characteristic resonant frequency; and said sensing structure further comprises a relatively planar spiral antenna bonded to said structural element and coupled to an electrochemical cell and a timing circuit, said interrogation electromagnetic field is so applied by generating electromagnetic pulses emitted from said antenna at pre-determined intervals for said remote measurement thereof by said receiver; and a pre-correlation made between a series of resonant frequency values taken for said sensing structure and a corresponding series of analyte sensing values is used for the sensing; and said characteristic resonant frequency value corresponds with a relative maximum of said plurality of successive values for electromagnetic emission intensity.

6. A resonant sensing apparatus for operative arrangement within an environment to sense an analyte, comprising:

a sensing structure comprising an antenna in electrical communication with a resonant circuit at least one component of which has a structural element made of a material that selectively responds to the analyte, said antenna coupled to an electro-chemical cell and a timing circuit to emit electromagnetic energy over an operating range of interrogation frequencies;

a remote receiver for measurement of a plurality of values for said electromagnetic emission intensity to identify a characteristic resonant frequency for said sensing structure in the presence of the analyte; and a pre-correlation made between a series of resonant frequency values taken for said sensing structure and a corresponding series of analyte sensing values.

7. The apparatus of claim 6 wherein: said material is a chemically receptive polymer, said selective response comprises absorption of subatomic particulate matter from the analyte for sensing presence thereof within the environment; said electromagnetic energy is so emitted as a plurality of electromagnetic pulses; and said plurality of values for electromagnetic emission intensity comprise a plurality of successive values taken over said operating range.

8. The apparatus of claim 6 wherein: said at least one component comprises electrically-isolated first and second conductive segments adhered to a first side of said structural element; and said electromagnetic energy is so emitted such that said plurality of values for electromagnetic emission intensity comprise a plurality of successive values taken over said operating range.

9. The apparatus of claim 8 wherein: said first and second conductive segments are patterned onto said first side; and said selective response comprises a chemical interaction with the analyte for sensing presence thereof; and said sensing structure further comprises a magnetizable on-off switch made of a magnetically hard element which, when activated, causes said characteristic resonant frequency to fall outside of a predetermined operating range of frequencies.

10. The apparatus of claim 6 wherein the analyte is glucose, said material is a polymer having a plurality of swellable gel membrane complexes, said selective response comprises diffusion of selected ion species of the analyte into said polymer, and said corresponding series of analyte sensing values comprises glucose concentration values.

11. The apparatus of claim 6 wherein said material is a polymer hydrogel having a plurality of microspheres reactive to electrostatic forces of subatomic particles within the analyte, said selective response causes a change in electrical characteristics of said resonant circuit; and the analyte is in liquid form.

12. The apparatus of claim 6 wherein the analyte is a gas comprising subatomic particles, said material has an outer zeolite layer, said selective response comprises interaction with at least a portion of said subatomic particles to cause a gain in matter of said zeolite layer causing a change in electrical characteristics of said resonant circuit.

* * * * *